(12) United States Patent
Gillies et al.

(10) Patent No.: US 9,218,752 B2
(45) Date of Patent: Dec. 22, 2015

(54) SYSTEM, METHOD, AND COMPUTER PROGRAM PRODUCT FOR SIMULATING EPICARDIAL ELECTROPHYSIOLOGY PROCEDURES

(75) Inventors: George Gillies, Charlottesville, VA (US); Harutyun V. Gyurjyan, Seaford, VA (US); Srijoy Mahapatra, Charlottesville, VA (US); Jason M. Tucker-Schwartz, Nashville, TN (US)

(73) Assignee: UNIVERSITY OF VIRGINIA PATENT FOUNDATION, Charlottesville, VA (US)

( * ) Notice: Subject to any disclaimer, the term of this patent is extended or adjusted under 35 U.S.C. 154(b) by 415 days.

(21) Appl. No.: 13/579,882

(22) PCT Filed: Feb. 18, 2011

(86) PCT No.: PCT/US2011/025470
§ 371 (c)(1),
(2), (4) Date: Nov. 29, 2012

(87) PCT Pub. No.: WO2011/103456
PCT Pub. Date: Aug. 25, 2011

(65) Prior Publication Data
US 2013/0108999 A1  May 2, 2013

Related U.S. Application Data

(60) Provisional application No. 61/305,560, filed on Feb. 18, 2010, provisional application No. 61/442,836, filed on Feb. 15, 2011.

(51) Int. Cl.
| | |
|---|---|
| *G09B 23/28* | (2006.01) |
| *G09B 23/30* | (2006.01) |
| *A61B 18/14* | (2006.01) |

(52) U.S. Cl.
CPC .............. *G09B 23/303* (2013.01); *G09B 23/28* (2013.01); *G09B 23/30* (2013.01); *A61B 18/1492* (2013.01)

(58) Field of Classification Search
USPC .......................................................... 434/262
See application file for complete search history.

(56) References Cited

U.S. PATENT DOCUMENTS

| | | | |
|---|---|---|---|
| 3,794,026 A | | 2/1974 | Jacobs |
| 3,808,706 A | * | 5/1974 | Mosley et al. ............... 73/865.9 |

(Continued)

FOREIGN PATENT DOCUMENTS

| | | |
|---|---|---|
| AU | 70522/96 | 1/1997 |
| CA | 2236958 | 5/1998 |

(Continued)

OTHER PUBLICATIONS

International Search Report corresponding to the PCT/US2011/025470 application.

(Continued)

*Primary Examiner* — Robert J Utama
(74) *Attorney, Agent, or Firm* — Robert J. Decker; Kilpatrick Townsend & Stockton LLP

(57) ABSTRACT

An aspect of various systems and methods provides, but not limited thereto, novel means for simulating physiological systems and processes in vitro in order to test surgical devices and train practitioners in the use of surgical devices. An aspect of various embodiments further provides in vitro anatomical components, such as a thorax, lungs, heart and pericardium, configured to contain at least one fluid having a pressure-frequency profile that may mimic typical pressure-frequency waveforms of in vivo anatomical fluids. A model communication system may be used to communicate the desired pressure-frequency profiles to the in vitro anatomical fluids. In a further aspect of various embodiments, an access device, e.g. a surgical instrument, configured to sense pressure, frequency, and/or a pressure-frequency profile may be inserted into one or more anatomical components of the in vitro model in order to test the instrument and/or train a practitioner in proper use of the instrument. An access device communication system may be used to communicate data to the practitioner. This data may include, for example, pressure-frequency data and/or the location of a portion of the access device with respect to the various in vitro anatomical components.

18 Claims, 29 Drawing Sheets

(56) References Cited

U.S. PATENT DOCUMENTS

| | | | | |
|---|---|---|---|---|
| 4,167,070 A | * | 9/1979 | Orden | 434/272 |
| 4,349,023 A | | 9/1982 | Gross | |
| 4,607,644 A | | 8/1986 | Pohndorf | |
| 4,817,634 A | | 4/1989 | Holleman | |
| 4,971,070 A | | 11/1990 | Holleman | |
| 4,991,603 A | | 2/1991 | Cohen | |
| 5,033,477 A | | 7/1991 | Chin | |
| 5,071,428 A | | 12/1991 | Chin | |
| 5,176,153 A | * | 1/1993 | Eberhardt | 128/897 |
| 5,213,570 A | | 5/1993 | VanDeripe | |
| 5,269,326 A | | 12/1993 | Verrier | |
| 5,300,110 A | | 4/1994 | Latterell | |
| 5,335,313 A | | 8/1994 | Douglas | |
| 5,336,252 A | | 8/1994 | Cohen | |
| 5,395,349 A | | 3/1995 | Quiachon | |
| 5,465,711 A | | 11/1995 | Moll | |
| 5,484,423 A | | 1/1996 | Waskonig | |
| 5,509,924 A | | 4/1996 | Paspa | |
| 5,544,654 A | | 8/1996 | Murphy | |
| 5,669,882 A | | 9/1997 | Pyles | |
| 5,679,005 A | | 10/1997 | Einstein | |
| 5,702,438 A | | 12/1997 | Avitall | |
| 5,725,504 A | | 3/1998 | Collins | |
| 5,733,280 A | | 3/1998 | Avitall | |
| 5,779,699 A | | 7/1998 | Lipson | |
| 5,797,870 A | | 8/1998 | March | |
| 5,800,428 A | | 9/1998 | Nelson | |
| 5,812,978 A | | 9/1998 | Nolan | |
| 5,827,216 A | | 10/1998 | Igo | |
| 5,843,048 A | | 12/1998 | Gross | |
| 5,846,239 A | | 12/1998 | Swanson | |
| 5,885,217 A | | 3/1999 | Gisselberg | |
| 5,899,937 A | * | 5/1999 | Goldstein et al. | 623/2.11 |
| 5,916,194 A | | 6/1999 | Jacobsen | |
| 5,931,810 A | | 8/1999 | Grabek | |
| 5,970,457 A | | 10/1999 | Brant | |
| 5,972,013 A | | 10/1999 | Schmidt | |
| 6,036,685 A | | 3/2000 | Mueller | |
| 6,051,008 A | | 4/2000 | Saadat | |
| 6,062,866 A | * | 5/2000 | Prom | 434/268 |
| 6,123,084 A | | 9/2000 | Jandak | |
| 6,148,825 A | | 11/2000 | Anderson | |
| 6,156,009 A | | 12/2000 | Grabek | |
| 6,156,018 A | | 12/2000 | Hassett | |
| 6,162,195 A | | 12/2000 | Igo | |
| 6,200,303 B1 | | 3/2001 | Verrior | |
| 6,206,004 B1 | | 3/2001 | Schmidt | |
| 6,231,518 B1 | | 5/2001 | Grabek | |
| 6,234,804 B1 | | 5/2001 | Yong | |
| 6,237,605 B1 | | 5/2001 | Vaska | |
| 6,263,241 B1 | | 7/2001 | Rosborough | |
| 6,266,567 B1 | | 7/2001 | Ishikawa | |
| 6,270,476 B1 | | 8/2001 | Santoianni | |
| 6,270,484 B1 | | 8/2001 | Yoon | |
| 6,273,877 B1 | | 8/2001 | West | |
| 6,278,975 B1 | | 8/2001 | Brant | |
| 6,314,963 B1 | | 11/2001 | Vaska | |
| 6,322,536 B1 | | 11/2001 | Rosengart | |
| 6,325,776 B1 | | 12/2001 | Anderson | |
| 6,416,505 B1 | | 7/2002 | Fleischman | |
| 6,423,051 B1 | | 7/2002 | Kaplan | |
| 6,443,735 B1 | * | 9/2002 | Eggert et al. | 434/262 |
| 6,500,130 B2 | | 12/2002 | Kinsella | |
| 6,527,767 B2 | | 3/2003 | Wang | |
| 6,551,289 B1 | | 4/2003 | Higuchi | |
| 6,554,809 B2 | | 4/2003 | Aves | |
| 6,558,382 B2 | | 5/2003 | Jahns | |
| 6,569,082 B1 | | 5/2003 | Chin | |
| 6,592,552 B1 | | 7/2003 | Schmidt | |
| 6,613,062 B1 | | 9/2003 | Leckrone | |
| 6,616,676 B2 | | 9/2003 | Bashiri | |
| 6,666,844 B1 | | 12/2003 | Igo | |
| 6,666,861 B1 | | 12/2003 | Grabek | |
| 6,689,128 B2 | | 2/2004 | Sliwa | |
| 6,711,436 B1 | | 3/2004 | Duhaylongsod | |
| 6,723,092 B2 | | 4/2004 | Brown | |
| 6,752,805 B2 | | 6/2004 | Maguire | |
| 6,771,996 B2 | | 8/2004 | Bowe | |
| 6,783,510 B1 | | 8/2004 | Gibson | |
| 6,786,898 B2 | | 9/2004 | Guenst | |
| 6,811,544 B2 | | 11/2004 | Schaer | |
| 6,827,714 B2 | | 12/2004 | Swanson | |
| 6,827,715 B2 | | 12/2004 | Francischelli | |
| 6,835,193 B2 | | 12/2004 | Epstein | |
| 6,837,848 B2 | | 1/2005 | Bonner | |
| 6,837,886 B2 | | 1/2005 | Collins | |
| 6,849,075 B2 | | 2/2005 | Bertolero | |
| 6,868,291 B1 | | 3/2005 | Bonner | |
| 6,869,414 B2 | | 3/2005 | Simpson | |
| 6,874,501 B1 | * | 4/2005 | Estetter et al. | 128/205.15 |
| 6,876,885 B2 | | 4/2005 | Swoyer | |
| 6,899,710 B2 | | 5/2005 | Hooven | |
| 6,916,318 B2 | | 7/2005 | Francischelli | |
| 6,918,890 B2 | | 7/2005 | Schmidt | |
| 6,918,908 B2 | | 7/2005 | Bonner | |
| 6,921,295 B2 | | 7/2005 | Sommer | |
| 6,928,313 B2 | | 8/2005 | Peterson | |
| 6,936,040 B2 | | 8/2005 | Kramm | |
| 6,960,205 B2 | | 11/2005 | Jahns | |
| 6,968,223 B2 | | 11/2005 | Hanover | |
| 6,973,352 B1 | | 12/2005 | Tsutsui | |
| 6,974,454 B2 | | 12/2005 | Hooven | |
| 7,004,937 B2 | | 2/2006 | Lentz | |
| 7,008,418 B2 | | 3/2006 | Hall | |
| 7,027,876 B2 | | 4/2006 | Casavant | |
| 7,037,296 B2 | | 5/2006 | Kadziauskas | |
| 7,041,099 B2 | | 5/2006 | Thomas | |
| 7,059,878 B1 | | 6/2006 | Hendrixson | |
| 7,063,693 B2 | | 6/2006 | Guenst | |
| 7,085,606 B2 | | 8/2006 | Flach | |
| 7,089,063 B2 | | 8/2006 | Lesh | |
| 7,090,637 B2 | | 8/2006 | Danitz | |
| 7,101,362 B2 | | 9/2006 | Vanney | |
| 7,104,986 B2 | | 9/2006 | Hovda | |
| 7,120,504 B2 | | 10/2006 | Osypka | |
| 7,130,699 B2 | | 10/2006 | Huff | |
| 7,142,919 B2 | | 11/2006 | Hine | |
| 7,146,225 B2 | | 12/2006 | Guenst | |
| 7,147,633 B2 | | 12/2006 | Chee | |
| 7,207,988 B2 | | 4/2007 | Leckrone | |
| 7,214,180 B2 | | 5/2007 | Chin | |
| 7,226,448 B2 | | 6/2007 | Bertolero | |
| 7,226,458 B2 | | 6/2007 | Kaplan | |
| 7,232,422 B2 | | 6/2007 | Gibson | |
| 7,247,139 B2 | | 7/2007 | Yudkovitch | |
| 7,259,906 B1 | | 8/2007 | Islam | |
| 7,264,587 B2 | | 9/2007 | Chin | |
| 7,286,992 B2 | | 10/2007 | Sander | |
| 7,309,328 B2 | | 12/2007 | Kaplan | |
| 7,398,781 B1 | | 7/2008 | Chin | |
| 7,468,029 B1 | | 12/2008 | Robertson | |
| 7,473,244 B2 | | 1/2009 | Frazier | |
| 2001/0020166 A1 | | 9/2001 | Daly | |
| 2001/0039410 A1 | | 11/2001 | Verrier | |
| 2002/0045895 A1 | | 4/2002 | Sliwa | |
| 2002/0055714 A1 | | 5/2002 | Rothschild | |
| 2002/0058925 A1 | | 5/2002 | Kaplan | |
| 2002/0072737 A1 | | 6/2002 | Belden | |
| 2002/0082523 A1 | | 6/2002 | Kinsella | |
| 2002/0161361 A1 | | 10/2002 | Sherman | |
| 2003/0028187 A1 | | 2/2003 | Vaska | |
| 2003/0065318 A1 | | 4/2003 | Pendekanti | |
| 2003/0069572 A1 | | 4/2003 | Wellman | |
| 2003/0114796 A1 | | 6/2003 | Schmidt | |
| 2003/0181855 A1 | | 9/2003 | Simpson | |
| 2004/0024397 A1 | | 2/2004 | Griffin | |
| 2004/0024413 A1 | | 2/2004 | Lentz | |
| 2004/0024435 A1 | | 2/2004 | Leckrone | |
| 2004/0033477 A1 | * | 2/2004 | Ramphal et al. | 434/272 |
| 2004/0034365 A1 | | 2/2004 | Lentz | |
| 2004/0064138 A1 | | 4/2004 | Grabek | |
| 2004/0087831 A1 | | 5/2004 | Michels | |
| 2004/0087938 A1 | | 5/2004 | Leckrone | |
| 2004/0102804 A1 | | 5/2004 | Chin | |

(56) References Cited

U.S. PATENT DOCUMENTS

| | | |
|---|---|---|
| 2004/0126746 A1 | 7/2004 | Toly |
| 2004/0138526 A1 | 7/2004 | Guenst |
| 2004/0138527 A1 | 7/2004 | Bonner |
| 2004/0138531 A1 | 7/2004 | Bonner |
| 2004/0147826 A1 | 7/2004 | Peterson |
| 2004/0176679 A1 | 9/2004 | Murphy et al. |
| 2004/0186507 A1 | 9/2004 | Hall |
| 2004/0215168 A1 | 10/2004 | Verrier |
| 2004/0216748 A1 | 11/2004 | Chin |
| 2004/0267303 A1 | 12/2004 | Guenst |
| 2004/0267326 A1 | 12/2004 | Ocel |
| 2005/0004514 A1 | 1/2005 | Hochman |
| 2005/0020914 A1 | 1/2005 | Amundson |
| 2005/0027243 A1 | 2/2005 | Gibson |
| 2005/0085769 A1 | 4/2005 | MacMahon |
| 2005/0154376 A1 | 7/2005 | Riviere |
| 2005/0215945 A1 | 9/2005 | Harris et al. |
| 2005/0234507 A1 | 10/2005 | Geske |
| 2005/0251094 A1 | 11/2005 | Peterson |
| 2005/0256368 A1 | 11/2005 | Klenk |
| 2005/0261673 A1 | 11/2005 | Bonner |
| 2005/0273006 A1 | 12/2005 | Stewart |
| 2005/0273144 A1 | 12/2005 | Lennox |
| 2006/0025705 A1 | 2/2006 | Whittaker |
| 2006/0025762 A1 | 2/2006 | Mohan |
| 2006/0041243 A1 | 2/2006 | Nayak |
| 2006/0052660 A1 | 3/2006 | Chin |
| 2006/0064056 A1 | 3/2006 | Coyle |
| 2006/0064058 A1 | 3/2006 | Coyle |
| 2006/0074397 A1 | 4/2006 | Shimada |
| 2006/0106442 A1 | 5/2006 | Richardson |
| 2006/0122591 A1 | 6/2006 | Keidar |
| 2006/0189840 A1 | 8/2006 | Walsh |
| 2006/0200002 A1 | 9/2006 | Guenst |
| 2006/0229490 A1 | 10/2006 | Chin |
| 2006/0247522 A1 | 11/2006 | McGee |
| 2006/0247672 A1 | 11/2006 | Vidlund |
| 2006/0259017 A1 | 11/2006 | Heil |
| 2006/0270900 A1 | 11/2006 | Chin |
| 2006/0271032 A1 | 11/2006 | Chin |
| 2007/0016068 A1 | 1/2007 | Grunwald |
| 2007/0016069 A1 | 1/2007 | Grunwald |
| 2007/0016070 A1 | 1/2007 | Grunwald |
| 2007/0016072 A1 | 1/2007 | Grunwald |
| 2007/0032796 A1 | 2/2007 | Chin-Chen |
| 2007/0038052 A1 | 2/2007 | Swoyer |
| 2007/0043397 A1 | 2/2007 | Ocel |
| 2007/0055142 A1 | 3/2007 | Webler |
| 2007/0198041 A1 | 8/2007 | Rupp |
| 2007/0270882 A1 | 11/2007 | Hjelle |
| 2008/0015625 A1 | 1/2008 | Ventura |
| 2008/0051671 A1 | 2/2008 | Broome |
| 2008/0091109 A1 | 4/2008 | Abraham |
| 2008/0097399 A1 | 4/2008 | Sachar |
| 2008/0108945 A1 | 5/2008 | Kaplan |
| 2008/0183080 A1 | 7/2008 | Abraham |
| 2008/0208184 A1 | 8/2008 | Davies |
| 2008/0262432 A1 | 10/2008 | Miller |
| 2008/0294174 A1 | 11/2008 | Bardsley |
| 2009/0068627 A1 | 3/2009 | Toly |
| 2009/0069697 A1 | 3/2009 | Frazier |
| 2009/0246747 A1 | 10/2009 | Buckman, Jr. |
| 2009/0253102 A1 | 10/2009 | Porikli et al. |
| 2009/0311656 A1 | 12/2009 | Lundback et al. |
| 2010/0094143 A1 | 4/2010 | Mahapatra |
| 2010/0114093 A1 | 5/2010 | Mahapatra |
| 2010/0167251 A1* | 7/2010 | Boutchko et al. ............ 434/267 |
| 2010/0211064 A1 | 8/2010 | Mahapatra |
| 2010/0241185 A1 | 9/2010 | Mahapatra |
| 2012/0249890 A1 | 10/2012 | Chardon et al. |
| 2012/0274863 A1 | 11/2012 | Chardon et al. |
| 2012/0278348 A1 | 11/2012 | Chardon et al. |
| 2012/0283582 A1 | 11/2012 | Mahapatra et al. |
| 2012/0310052 A1 | 12/2012 | Mahapatra |
| 2012/0330184 A1 | 12/2012 | Mahapatra |

FOREIGN PATENT DOCUMENTS

| | | |
|---|---|---|
| DE | 43 13 903 C1 | 9/1994 |
| EP | 0 450 608 A1 | 10/1991 |
| EP | 1 129681 | 9/2001 |
| EP | 1 181 896 | 2/2002 |
| WO | WO 87/04081 | 7/1987 |
| WO | WO 93/20878 | 10/1993 |
| WO | WO 93/20886 | 10/1993 |
| WO | WO 95/10319 | 4/1995 |
| WO | WO 95/15115 | 6/1995 |
| WO | WO 97/33526 | 9/1997 |
| WO | WO 99/18869 | 4/1999 |
| WO | WO 01/05306 | 1/2001 |
| WO | WO 01/58373 | 8/2001 |
| WO | WO 01/68173 | 9/2001 |
| WO | WO 01/80724 | 11/2001 |
| WO | WO 01/80757 | 11/2001 |
| WO | WO 01/93930 | 12/2001 |
| WO | WO 2008/112870 | 9/2008 |
| WO | WO 2008/115745 | 9/2008 |
| WO | WO 2008/118737 | 10/2008 |
| WO | WO 2009/062061 | 5/2009 |
| WO | WO 2011/103456 | 8/2011 |

OTHER PUBLICATIONS

U.S. Appl. No. 61/305,560, filed Feb. 18, 2010.
U.S. Appl. No. 61/442,836, filed Feb. 15, 2011.
Stokes, U.S. Statutory Invention Registration H356, Nov. 3, 1987.
DP25B-S Strain Gage Pagel Meter: User's Guide, OMEGA Engineering, Inc., 2002 (accessed Jul. 9, 2007), Stamford, CT. Online at http://vvww.omega.com/Manuals/manualpdf/M3598.pdf.
DP41B Universal Input Meter: User's Guide, OMEGA Engineering, Inc., 2005 (accessed Dec. 5, 2007), Stamford, CT. Online at http://vvww.omega.com/Manuals/manualpdf.M2544.pdf.
DPI 603 Portable Pressure Calibrator User Guide, OMEGA Engineering, Inc., 1996 (accessed Dec. 5, 2007), Stamford, CT. Online at http://vvww.omega.com/Manuals/manual.pdf/M2913.pdf.
PX26 Series Pressure Transducers: Instruction Sheet, OMEGA Engineering, Inc., 2004 (accessed Jul. 9, 2007), Stamford, CT. Online at http//www.omega.com/Pressure/pdf/PX26.pdf.
PX26 Series Pressure Transducers: Instruction Sheet, Omega Engineering, Inc., 2004 (accessed Dec. 5, 2007), Stamford, CT. Online at http://vvww.omega.com/Manuals/manualpdf/M1608.pdf.
Arrow International Corporation, AN-05505 Epidural Needle, vvww.arrowintl.com/products/boms/AN05505.asp?cat=17 &item=AN-05505&xsec= {accessed Feb. 13, 2007).
Beukema, "Radiofrequency Ablation of Atrial Fibrillation in Patients Undergoing Concommitant Cardiac Surgery. First Experience," PACE, 1997, p. 1100, vol. 20 (Part II).
D'Avila, "Transthoracic Epicardial Catheter Ablation of Ventricular Tachycardia," Heart Rhythmn, 2006, p. 1110-1111, vol. 3.
Derose, Jr., "Robotically Assisted Left Ventricular Epicardial Lead Implantation for Biventricular Pacing: the Posterior Approach," The Annals of Thoracic Surgery, 2004, p. 1472-1474, vol. 77.
Frölich, "Pioneers in Epidural Needle Design," Anesthesia & Analgesia, 2001, p. 215-220, vol. 93.
Hansky, "Lead Selection and Implantation Technique for Biventricular Pacing," European Heart Journal Supplements, 2004, p. D112-D116, vol. 6, Supplement D.
Klein, "Radiofrequency Ablation of Cardiac Arrhythmias," Scientific American Science & Medicine, 1994, p. 48-57.
Lin, "Catheter Microwave Ablation Therapy for Cardiac Arrhythmias," Bioelectromagnetics, 1999, p. 120-132, vol. 20.
Mahapatra, "Access Device and Manometric Monitoring System for Epicardial Electrophysiology: Improved Porototype and Use in Human Trials", Jul. 2007, Technical Report No. UVA/640419/MAE08/101.
Mahapatra, "Access Device and Manometric Monitoring System for Epicardial Electrophysiology: Improved Porototype and Use in Human Trials", Jan. 2008, Technical Report No. UVA/640419/MAE08/102.

(56) References Cited

OTHER PUBLICATIONS

Mahapatra, "Incidence and Predictors of Cardiac Perforation after Permanent Pacemaker Placement," Heart Rhythm, 2005, p. 907-911, vol. 2, No. 9.

Mair, "Epicardial Lead Implantation Techniques for Biventricular Pacing via Left Lateral Mini-Thoracotomy, Video- Assisted Thoracoscopy, and Robotic Approach," The Heart Surgery Forum #2003-4883, 2003, p. 412-417, vol. 6 (5).

Moses, "Sirolimus-Eluting Stents Versus Standard Stents in Patients with Stenosis in a Native Coronary Artery", New England Journal of Medicine, 2003, p. 1315-1323, vol. 349, No. 14.

Packer, "Multimodality 3-D Ultrasound and Computed Tomographic Image Fusion: A Novel Basis for Catheter Navigation and Electroanatomic Mapping," 2005, Circulation, Clinical Science, Supplement 11, vol. 112, No. 17, #2939.

Sarabanda, "Efficacy and Safety of Circumferential Pulmonary Vein Isolation Using a Novel Cryothermal Balloon Ablation System" Journal of the American College of Cardiology, 2005, p. 1902-1912, vol. 46, No. 10.

Sosa, "Epicardial Mapping and Ablation Techniques to Control Ventricular Tachycardia,"Journal of Cardiovascular Electrophysiology, 2005, p. 449-452, vol. 16, No. 4.

Sosa, "Nonsurgical Transthoracic Epicardial Approach in Patients with Ventricular Tachycardia and Previous Cardiac Surgery," Journal of Interventional Cardiac Electrophysiology, 2004, p. 281-288, vol. 10.

Sosa, "Percutaneous Pericardia! Access for Mapping and Ablation of Epicardial Ventricular Tachycardias," Circulation, Journal of the American Heart Association, 2007, p. e542-e544, vol. 115.

Thomas, "Analysis of Human Epidural Pressures," Regional Anesthesia, 1992, p. 212-215, vol. 17, No. 4.

Tomaske, "Do Daily Threshold Trend Fluctuations of Epicardial Leads Correlate with Pacing and Sensing Characteristics in Paediatric Patients," Europace, 2007, p. 662-668, vol. 9.

J. Tucker-Schwartz et al., "Improved Pressure-Frequency Sensing Subxiphoid Pericardial Access System: Performance Characteristics During in Vivo testing," IEEE Transactions on Biomedical Engineering, vol. 58, pp. 845-852 (Apr. 2011).

J. Tucker-Schwartz et al., "Pressure-Frequency Sensing Subxiphoid Access System for Use in Percutaneous Cardiac Electrophysiology: Prototype Design and Pilot Study Resutls," IEEE Transactions on Biomedical Engineering, vol. 56, pp. 1160-1168 (May 2009).

F. Sacher, P. Maury, I. Nault, M. Wright, N. Lellouche, N. Derval, S. Ploux, M. Hocini, P. Bordachar, A. Deplagne, P. Ritter, J. Clementy, M. Haissaguerre, and P. Jais, "Prevalence of epicardial scar in patients referred for ventricular tachycardia ablation," *Heart Rhythm*, vol. 6, pp. S175-S176, 2009.

C. Grimard, J. Lacotte, F. Hidden-Lucet, G. Duthoit, Y. Gallais, and R. Frank, "Percutaneous epicardial radiofrequency ablation of ventricular arrhythmias after failure of endocardial approach: a 9-year experience," *J. Cardiovasc. Electrophysiol.*, vol. 21, No. 1, pp. 56-61, 2010.

E. Aliot, W. Stevenson, J. Almendral-Garrote, F. Bogun, C. Calkins, E. Delacretaz, P. Bella, G. Hindricks, P. Jais, M. Josephson, J. Kautzner, G. Kay, K. Kuck, B. Lerman, F. Marchlinski, V. Reddy, M. Schalij, R. Schilling, L. Soejima, and D. Wilber, "EHRA/HRS expert consensus on catheter albation of ventricular arrhythmias," *Europace*, vol. 11, No. 6, pp. 771-817, 2009.

E. Sosa, M. Scanavacca, A. d'Avila, and F. Pilleggi, "A new technique to perform epicardial mapping in the electrophysiology laboratory," *J. Cardiovasc. Electrophysiol.*, vol. 7, No. 6, pp. 531-536, 1996.

E. Sosa, M. Scanavacca, A. d'Avila, J. Piccioni, O. Sanchez, J. Velarde, M. Silva, and B. Reolao, "Endocardial and epicardial ablation guided by nonsurgical transthoracic epicardial mapping to treat recurrent ventricular tachycardia," *J. Cardiovasc. Electrophysiol.*, vol. 9, No. 3, pp. 229-239, 1998.

E. Sosa, M. Scanavacca, A. d'Avila, F. Oliviera, and J. Ramires, "Nonsurgical transthoracic epicardial catheter ablation to treat recurrent ventricular tachycardia occuring late after myocardial infarction," *J. Am. Coll. Cardiol.*, vol. 35, No. 6, pp. 1442-1449, 2000.

U. Tedrow and W. Stevenson, "Strategies for epicardial mapping and ablation of ventricular tachycardia," *J. Cardiovasc. Electrophysiol.*, vol. 20, No. 6, pp. 710-713, 2009.

S. Mahapatra, J. Tucker—Schwartz, D. Wiggins, G. Gillies, P. Mason, G. McDaniel, D. Lapar, C. Stemland, E. Sosa, J. Ferguson, T. Bunch, G. Ailawadi, and M. Scanavacca, "Pressure frequency characteristics of the pericardial space and thorax during subxiphoid access for epicardial ventricular tachycardia ablation," *Heart Rhythm*, vol. 7, No. 5, pp. 604-609, 2010.

Office Action in U.S. Appl. No. 13/607,993 mailed Aug. 14, 2014.
Office Action in U.S. Appl. No. 13/464,752 mailed Dec. 4, 2014.
Office Action in U.S. Appl. No. 13/464,762 mailed May 4, 2012.

\* cited by examiner

| Wave | 1 | 2 | 3 | 4 | 5 | 6 |
|---|---|---|---|---|---|---|
| Run 1 'ρ' | 0.9880 | 0.9800 | 0.9927 | 0.9986 | 0.9981 | 0.9862 |
| Run 2 'ρ' | 0.9958 | 0.9851 | 0.9970 | 0.9926 | 0.9984 | 0.9844 |
| Run 3 'ρ' | 0.9979 | 0.9856 | 0.9942 | 0.9897 | 0.9928 | 0.9844 |
| Run 4 'ρ' | 0.9952 | 0.9854 | 0.9947 | 0.9986 | 0.9948 | 0.9836 |
| Average 'ρ' | 0.9942 | 0.9840 | 0.9947 | 0.9949 | 0.9960 | 0.9846 |
| 'ρ' St Dev | 0.0043 | 0.0027 | 0.0018 | 0.0045 | 0.0027 | 0.0011 |

FIG. 13

SYSTEM, METHOD, AND COMPUTER PROGRAM PRODUCT FOR SIMULATING EPICARDIAL ELECTROPHYSIOLOGY PROCEDURES

RELATED APPLICATIONS

This application is a national stage application of, and claims priority to, International Application No. PCT/US2011/025470 filed Feb. 18, 2011, which claims priority from U.S. Provisional Application Ser. No. 61/305,560, filed Feb. 18, 2010 and U.S. Provisional Application Ser. No. 61/442,836, filed Feb. 15, 2011, the disclosures of which are hereby expressly incorporated herein by reference in their entirety.

FIELD OF THE INVENTION

Some of the embodiments of the invention are, but not limited thereto, in the field of anatomical and physiological simulation systems. More specifically, some of the embodiments of invention may be in the field of means and methods for simulating interventional procedures in such a way as to train electrophysiologists and test electrophysiological instrumentation using a simulator as the model. Still more specifically, some of the embodiments of the invention may be in the sub-field of simulating the pressure-sensed intrathoracic navigation of a surgical probe, instrument, device, or other type of medical means or instruments within a subject following sub-xyphoid insertion, with the intention of safely reaching the epicardial surface of the heart.

BACKGROUND OF THE INVENTION

Simulators used for medical education and training purposes do not allow for (among other things) the simulation of the unique pressure-frequency relationship that has been observed in the pericardial fluid, and which is taken advantage by the Applicant for the safe intrathoracic navigation of a probe onto the epircardial surface to help enable electrophysiological procedures, as described in the Applicant's related applications: 1. PCT International Application No. Serial No. PCT/US2008/056643, filed Mar. 12, 2008, entitled, "Access Needle Pressure Sensor Device and Method of Use" and corresponding U.S. patent application Ser. No. 12/530,830 filed Sep. 11, 2009; 2. PCT International Application No. Serial No. PCT/US2008/056816, filed Mar. 13, 2008, entitled, "Epicardial Ablation Catheter and Method of Use" and corresponding U.S. patent application Ser. No. 12/530,938 filed Sep. 11, 2009; 3. PCT International Application No. Serial No. PCT/US2008/057626, filed Mar. 20, 2008, entitled, "Electrode Catheter for Ablation Purposes and Related Method Thereof" and corresponding U.S. patent application Ser. No. 12/532,233 filed Sep. 21, 2009; and 4. PCT International Application No. Serial No. PCT/US2008/082835, filed Nov. 7, 2008, entitled, "Steerable Epicardial Pacing Catheter System Placed Via the Subxiphoid Process," and corresponding U.S. patent application Ser. No. 12/741,710 filed May 6, 2010, all of which are incorporated by reference in their entirety.

Ventricular tachycardia is an often fatal heart arrhythmia that is responsible for roughly 500,000 deaths per year in the US alone. Radio-frequency thermal ablation can be used to treat this condition, as is also the case for atrial fibrillation which is a less lethal but even more wide-spread condition. At present, such ablations are typically carried out on the endocardial surface (inside the heart) via catheterization through the femoral artery. However, there are significant risks associated with such procedures, including stroke and thermal damage to the esophagus and phrenic nerve.

In a different approach, access to the epicardial surface is gained by needle-based sub-xyphoid puncture, with gentle movement of the tip through the diaphragm and into the pericardial space. Successful positioning at the epicardial surface is then confirmed via flush of contrast agent within the pericardium, thus revealing the cardiac silhouette on fluoroscopy. Thereafter, a guidewire is placed through the needle and into the pericardium. The needle is then removed, and a sheath is placed over the guidewire to allow for passage of the ablation catheter to treat the electrically misfiring zones of myocardial tissue.

While a safe and workable technique in skilled hands, there is a learning curve involved and the most significant risk associated with it is inadvertent penetration of the right ventricle by the access needle, a situation that calls for immediate surgical intervention to seal the perforation. In order to minimize this risk, in related patent applications (See 1. PCT International Application No. Serial No. PCT/US2008/056643, filed Mar. 12, 2008, entitled, "Access Needle Pressure Sensor Device and Method of Use" and corresponding U.S. patent application Ser. No. 12/530,830 filed Sep. 11, 2009; 2. PCT International Application No. Serial No. PCT/US2008/056816, filed Mar. 13, 2008, entitled, "Epicardial Ablation Catheter and Method of Use" and corresponding U.S. patent application Ser. No. 12/530,938 filed Sep. 11, 2009; 3. PCT International Application No. Serial No. PCT/US2008/057626, filed Mar. 20, 2008, entitled, "Electrode Catheter for Ablation Purposes and Related Method Thereof" and corresponding U.S. patent application Ser. No. 12/532,233 filed Sep. 21, 2009; and 4. PCT International Application No. Serial No. PCT/US2008/082835, filed Nov. 7, 2008, entitled, "Steerable Epicardial Pacing Catheter System Placed Via the Subxiphoid Process," and corresponding U.S. patent application Ser. No. 12/741,710 filed May 6, 2010.), the Applicant has introduced the concept of pressure-frequency monitoring at the needle's tip. By incorporating a pressure sensor within the distal tip of the needle, the slow steady ac signal associated with the breathing rate of the intubated patients (typically 11 to 12 breaths per minute) is detected while the needle is within the thorax. Then, when the needle's tip arrives at and enters the pericardium, a higher frequency component (at the heart rate, 60 to 90 beats per minute) is superimposed on the lower frequency one. A real-time spectral analysis or beat-to-beat analysis of the signal during the access procedure can thus provide the clinician with a "stop/go" indicator that will keep them from advancing the needle too far and perforating the heart.

Accordingly, an aspect of an embodiment of the present invention provides, but not limited thereto, the ability to train physicians to replace the existing qualitative approach of needle navigation with a decidedly quantitative one, thus making it possible for electrophysiologists to do this procedure more routinely.

BRIEF SUMMARY OF THE INVENTION

Pressure-sensitive instrumentation can be used to monitor a range of physiological measurements, including those of interest in cardiology. However, the utility of such pressure-sensing systems in the clinical setting must be firmly established and well tested before introduction into approved routine use. Accordingly, Applicant herein provides the ability to mimic real patient hydrodynamic pressure waveforms outside of the clinic to test both instrumentation and software performance in a realistic scenario, and also the ability to create in vitro anatomical pressure chambers, which can be used for both testing of devices and clinical training.

Accordingly, an aspect of an embodiment of the present invention provides, among other things, an anatomical training and testing tool, in vitro system, which creates hydrodynamic pressures in a cavity that simulate those found in the thoracic and pericardial cavities of a patient as seen in epicardial access procedures. During epicardial access for electrophysiology procedures, providing pressure-frequency guidance would be a novel tool for quantitatively notifying to the clinician when they have entered the extremely thin pericardial target for instrumentation. However, such a procedure, and use of fluid filled pressure-sensing systems and their accompanying data acquisition and processing systems, require experience and the ability to test the devices before being brought into the clinic. Accordingly, an aspect of an embodiment of the present invention provides, among other things, an in vitro system and method for mimicking the waveforms experienced during epicardial access in the hopes of applying dynamic pressure chambers to anatomical testing tools.

Moreover, it is difficult to find effective means for creating programmable arbitrary pressure waveforms in a chamber or cavity to create in vitro pressure testing scenarios, which have high resolution, control, and flexibility. Also, it is important to be able to add a component of noise to the scenario, to be able to test both ideal pressure waveforms, and non-ideal pressure waveforms, to ensure the robust characteristics of a given instrumentation and software system. Various embodiments of the present invention pressure-sensing simulation system and method presented herein provides, among other things, all these features as applied to epicardial access procedures.

For instance, in order to minimize the need for and costs of in vivo experimentation to test access needle prototypes, validate pressure-frequency analysis algorithms, and train physicians in this approach, an aspect of an embodiment of the present invention provides, among other things, anthropomorphic simulators (and related method) for epicardial procedures. Although there are mannequin-type simulators used in medical education and training programs today, current mannequin-type simulators do not provide for access techniques for epicardial procedures.

An aspect of various embodiments of the present invention system and method provide, but are not limited thereto, novel means for simulating physiological systems and processes in vitro in order to test surgical devices and train practitioners in the use of surgical devices. Thus, various embodiments of the invention provide a more cost effective, humane, and repeatable means for testing instruments and simulating in vivo procedures that are known in the prior art.

An aspect of an embodiment of the present invention provides the ability for the development of new tools specifically tailored towards sub-xyphoid, percutaneous entry and navigation to the pericardial space. An aspect of an embodiment of the present invention provides the ability to have a means of economically and quickly testing the tool. Also, an aspect of an embodiment of the present invention provides the ability for the development of such a simulation model that will give a certain sense of the access procedure to inexperienced practitioners. Through the development of this life size model, the feasibility of replicating the temporal pressure characteristics in the pericardial space and the thoracic cage is able to be evaluated. This effort is important in the further development of more advanced models for the purpose of simulating epicardial access procedures and related operations. An aspect of an embodiment of the present invention provides the ability for not only replicating the pressure characteristics, but also to come as close as possible to the real life anatomical features including the rib cage, diaphragm, positions of the lungs, and heart.

In an aspect of an embodiment, the present invention overcomes limitations of the prior art by, among other things, replicating the pressure-frequency characteristics observable in an in vivo surgical procedure. In another aspect of an embodiment, the invention not only mimics real patient pressure waveforms outside of the clinic to test both instrumentation and software performance in a realistic scenario, but also comes as close as possible to the real life anatomical features including the rib cage, diaphragm, positions of the lungs, and heart. In yet another aspect of embodiment, the invention may be used to replacing the existing qualitative approach to needle navigation in certain surgical procedures with a decidedly quantitative one, thus making it possible for electrophysiologists to do this procedure routinely in the lab.

An aspect of an embodiment provides an in vitro model system comprising a thoracic cavity, lungs disposed within the thoracic cavity, the lungs configured to contain a lung fluid having a lung pressure-frequency profile, and a heart disposed within the thoracic cavity, the heart configured to contain a cardiac fluid having a cardiac pressure-frequency profile. The embodiment further comprises a pericardium disposed within the thoracic cavity and configured to at least partially surround the heart, the pericardium configured to contain a pericardial fluid having a pericardial pressure-frequency profile.

An aspect of an embodiment provides an in vitro model system comprising a set of anatomical components configured to contain at least one fluid, at least one pressure-frequency profile, and a model communication system for providing the at least one pressure-frequency profile to the at least one fluid.

An aspect of an embodiment provides an in vitro modeling method comprising providing a thoracic cavity, providing lungs disposed within said thoracic cavity and containing a lung fluid, and applying a lung pressure-frequency profile to the lung fluid. The embodiment further comprises providing a heart disposed within said thoracic cavity and containing a cardiac fluid, applying a cardiac pressure-frequency profile to the cardiac fluid, providing a pericardium disposed within said thoracic cavity, wherein the pericardium at least partially surrounds the heart, and wherein said pericardium contains a pericardial fluid, and applying a pressure-frequency profile to the pericardial fluid.

An aspect of an embodiment provides an in vitro modeling method comprising providing a set of anatomical components configured to contain at least one fluid, providing at least one pressure-frequency profile, and providing a model communication system that provides the at least one pressure-frequency profile to the at least one fluid.

An aspect of an embodiment provides an in vitro model system comprising a software program that encodes an algorithm (e.g., computer software code, algorithmic model, firmware, hardware, or computer medium) which captures the unique pressure-frequency characteristics of a pericardial fluid, a set of in vitro anatomical and physiological models for the organs and processes within the thoracic cavity of humans, and a means for causing the software program to communicate with and to actuate physiologic-like effects in the models.

It should be appreciated that as discussed herein, a subject may be a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to human (e.g. rat, dog, pig, monkey), etc. It should be appreciated that the subject may be any applicable human patient, for example. Use of the term "patient" to describe various subjects herein below should be understood to be exemplary only. It should be understood that the systems and method discussed can apply to any subject.

An aspect of various embodiments (system, method and computer program product) provides, but not limited thereto, novel means for simulating physiological systems and processes in vitro in order to test surgical devices and train practitioners in the use of surgical devices. An aspect of various embodiments (system, method and computer program product) further provides in vitro anatomical components, such as a thorax, lungs, heart and pericardium, configured to contain at least one fluid having a pressure-frequency profile that may mimic typical pressure-frequency waveforms of in vivo anatomical fluids. A model communication system may be used to communicate the desired pressure-frequency profiles to the in vitro anatomical fluids. In a further aspect of various embodiments (system, method and computer program product), an access device, e.g. a surgical instrument, configured to sense pressure, frequency, and/or a pressure-frequency profile may be inserted into one or more anatomical components of the in vitro model in order to test the instrument and/or train a practitioner in proper use of the instrument. An access device communication system may be used to communicate data to the practitioner. This data may include, for example, pressure-frequency data and/or the location of a portion of the access device with respect to the various in vitro anatomical components.

These and other objects, along with advantages and features of various aspects of embodiments of the invention disclosed herein, will be made more apparent from the description, drawings and claims that follow.

BRIEF DESCRIPTION OF THE DRAWINGS

The foregoing and other objects, features and advantages of the present invention, as well as the invention itself, will be more fully understood from the following description of preferred embodiments, when read together with the accompanying drawings The accompanying drawings, which are incorporated into and form a part of the instant specification, illustrate several aspects and embodiments of the present invention and, together with the description herein, serve to explain the principles of the invention. The drawings are provided only for the purpose of illustrating select embodiments of the invention and are not to be construed as limiting the invention.

FIG. 7A is an exploded view. In FIG. 7B is a more fully constructed view including a user demonstrating an embodiment of an access device.

FIG. 13 is a table of correlation coefficients relating the pressure output waveform from various trial runs of an embodiment of an in vitro model system to the reference waveform.

DETAILED DESCRIPTION OF EXEMPLARY EMBODIMENTS

It should be appreciated that any of the components or modules referred to with regards to any of the present invention embodiments discussed herein, may be a variety of materials and/or composites as necessary or required. Still further, it should be appreciated that any of the components or modules (or combination thereof) may provide shape, size and volume contoured by adjusting its geometry and flexibility/rigidity according to the target location or anatomy (or region, including structure and morphology of any location) being treated.

Figure 1:
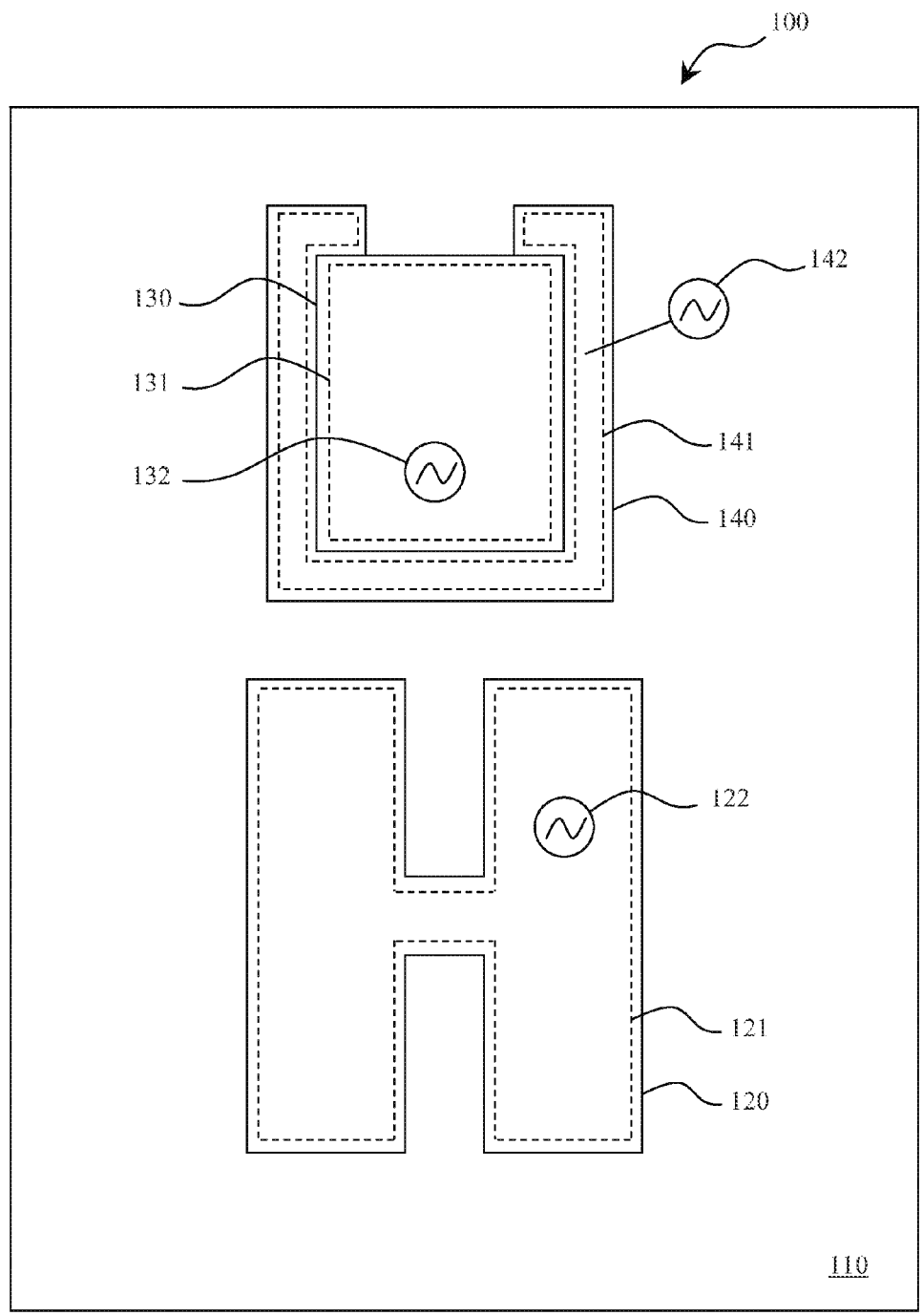
FIG. 1 is a schematic view of an embodiment of an in vitro model system comprising a thoracic cavity, lungs, a heart, and a pericardium.

FIG. 1 shows a schematic of an embodiment of the invention comprising an in vitro model system 100. The model system comprises a thoracic cavity 110 that houses lungs 120, a heart 130, and a pericardium 140 configured to at least partially the heart. The lungs, heart, and pericardium are configured to contain a lung fluid 121, a cardiac fluid 131, and a pericardial fluid 141, respectively. The organ fluids may be a liquid and/or a gas. For example, in a non-limiting aspect of an embodiment, the lung fluid may be air and the cardiac and pericardial fluids may both be water. However, it should be appreciated that the organ fluids could comprise any known liquid or gas that could be contained within an in vitro model organ. In another non-limiting example, the organ fluids may have properties that mimic body fluids such as blood or pericardial fluid.

Figure 10:
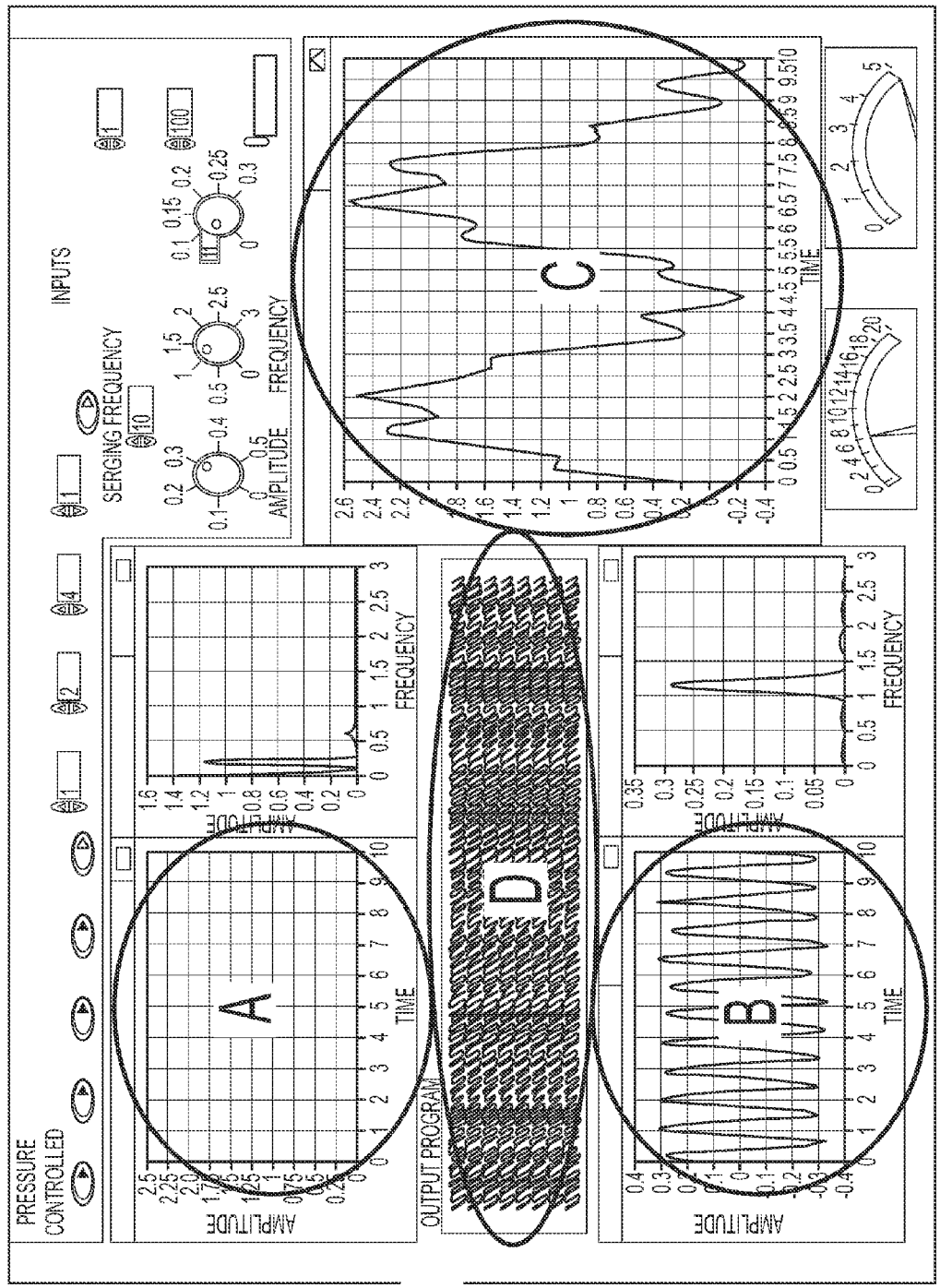
FIG. 10 is a computer-generated illustration of an interface used to create a pressure-frequency profile. The figure shows a time domain representations of a cardiac waveform component (A), a ventilation waveform (B), and a summed final pericardial waveform (C). Also shown is a compiled computer program (D), embodying the final pericardial waveform.
Figure 12:
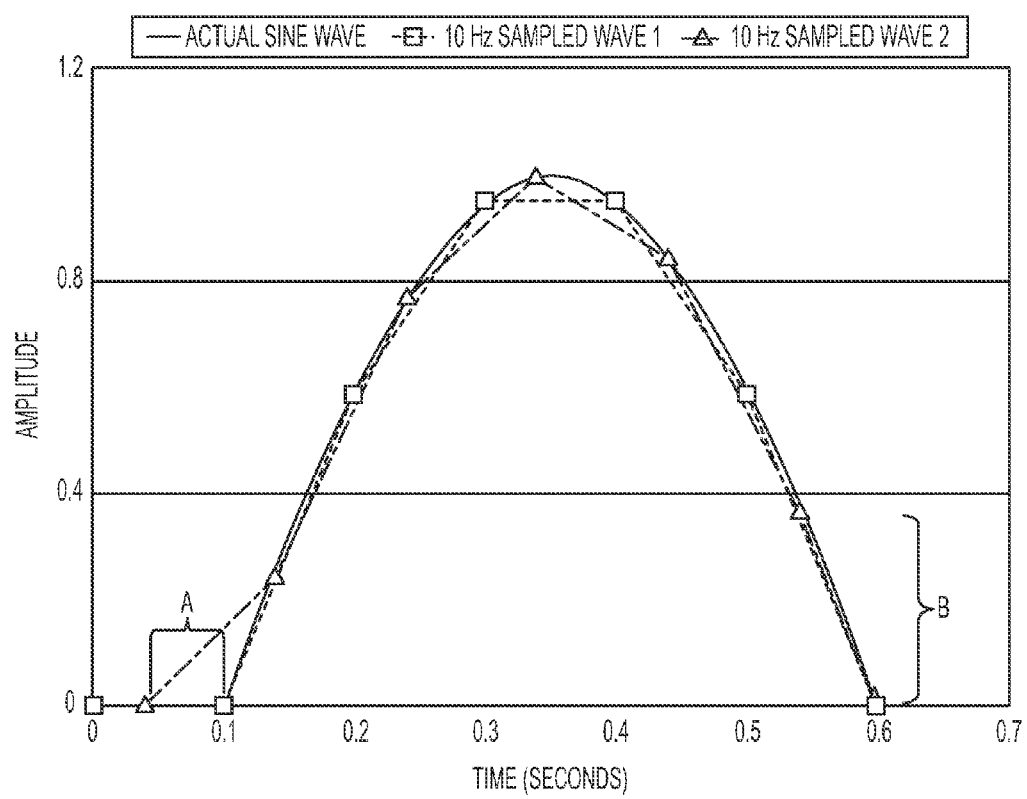
FIG. 12 is a graphical representation of a phase shift 'A' in the time domain between the two processes causing large amplitude differences such as 'B' between corresponding samples.

In the embodiment of FIG. 1, the hydrodynamic pressure characteristics of each organ fluid is configured to vary periodically as a function of time. Thus, the lung, cardiac, and pericardial fluids have pressure-frequency profiles 122, 132, and 142, respectively. The pressure-frequency profiles describe the pressure of the fluid contained in each organ as a function of time. Each pressure-frequency profile has a particular spectral structure, yielding a corresponding amplitude and frequency in the time domain. In an aspect of an embodiment, a pressure-frequency profile may be, for example, a sinusoidal profile. For example, the cardiac pressure-frequency profile may be sinusoidal. FIG. 12 includes an example of a sinusoidal pressure-frequency profile, labeled "actual sine wave" in the figure. Alternatively, a pressure-frequency profile may replicate any other periodic function, such as, for example, a square wave or triangle wave. Alternatively, a pressure-frequency profile may simulate or mimic a subject organ waveform, or a damped component thereof. For example, a lung pressure-frequency profile may mimic a subject breathing or intubation waveform, and a cardiac pressure-frequency profile may mimic a subject cardiac blood pressure waveform. The subject may be, for example, a human or any other animal. FIG. 10 depicts an illustrative non-limiting example in which the cardiac pressure-frequency profile (A) mimics a sinusoidal human cardiac waveform component, and the respiratory pressure-frequency profile (B) mimics a quasi-triangle human respiratory waveform.

Figure 9:
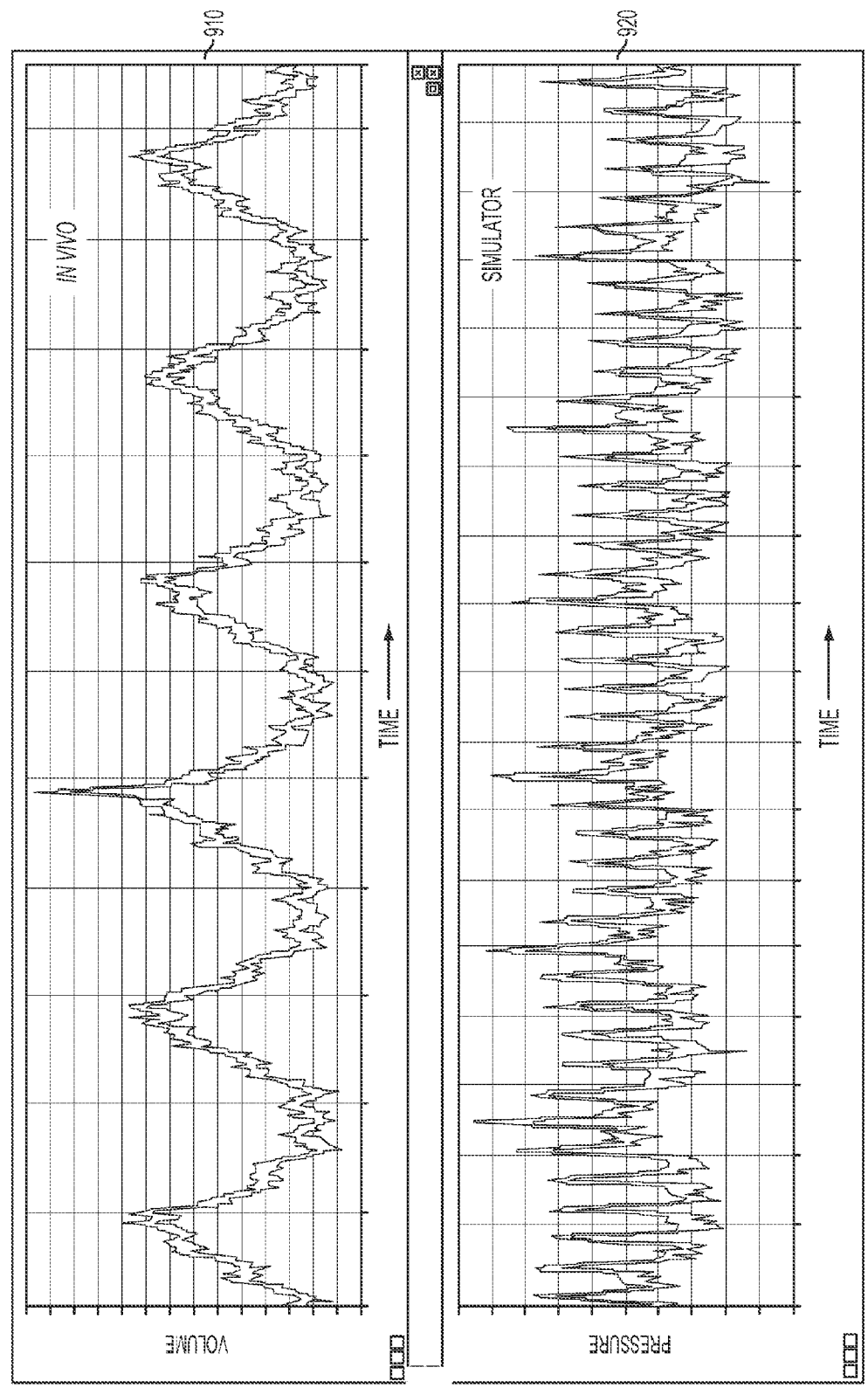
FIG. 9 is a computer-generated graph of two example pressure-frequency profiles.
Figure 23:
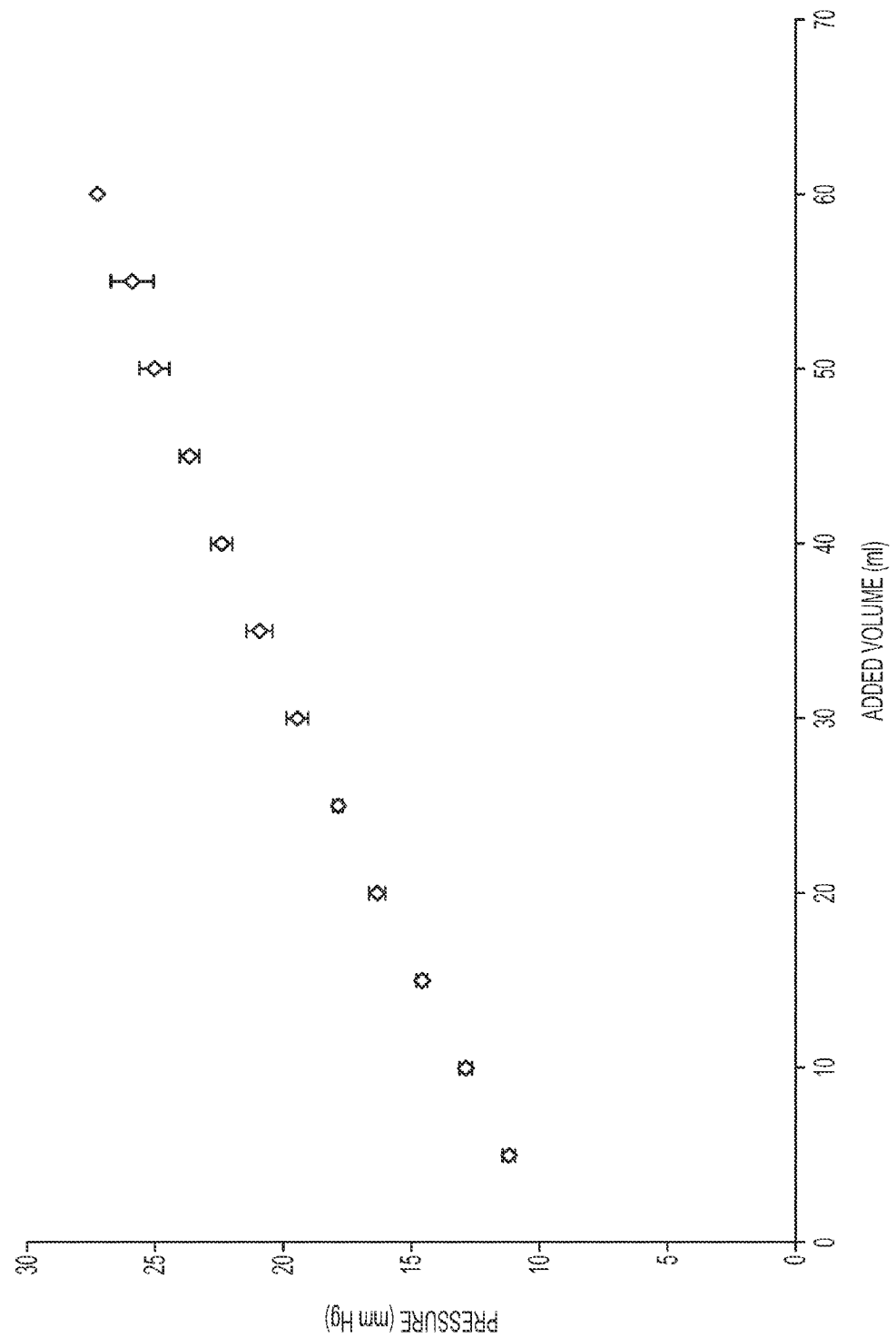
FIG. 23 is a graphical representation of the compliance of an embodiment of an in vitro heart model, showing the relationship between internal pressure and the change in volume.

It should also be appreciated that the pressure-frequency profile of a given organ could be expressed in terms of volume as a function of time, rather than pressure as a function of time. For example, one could measure the compliance of a particular in vitro organ, that is, the change in volume of the in vitro organ as a function of the pressure of the organ fluid. FIG. 23 provides an illustrative example of such a compliance function for a model in vitro organ. The measured rate of compliance might then be used to convert the pressure-frequency profile into units of volume as a function of time. FIG. 9, for example, provides an example of a pressure-frequency profile expressed as a volume as a function of time (FIG. 9A), and a second pressure-frequency profile expressed as a pressure as a function of time (FIG. 9B). Similarly, it should be appreciated that a pressure-frequency profile could be expressed in any unit of measurement where the relationship between pressure and the chosen unit of measurement is known. Alternatively, the pressure-frequency profile may even be a unitless waveform (see, for example, FIG. 12) that is later scaled to a desired measurement, such as a desired pressure amplitude.

The organ pressure-frequency profiles may all be, for example, independent from one another. Alternatively, one or more of the pressure-frequency profiles may be a dependent function of one or more of the other pressure-frequency profiles, or damped components thereof. For example, in one non-limiting aspect of an embodiment, the pericardial pressure-frequency profile may correspond to the sum of the lung pressure-frequency profile and a damped component of the cardiac pressure-frequency profile. FIG. 10 depicts such an example, in which the final pericardial pressure-frequency profile (C) is the sum of a damped component of the cardiac pressure-frequency profile (A) and the respiratory pressure-frequency profile (B). FIG. 9B depicts a second example of a summed pressure-frequency profile.

Figure 8A:
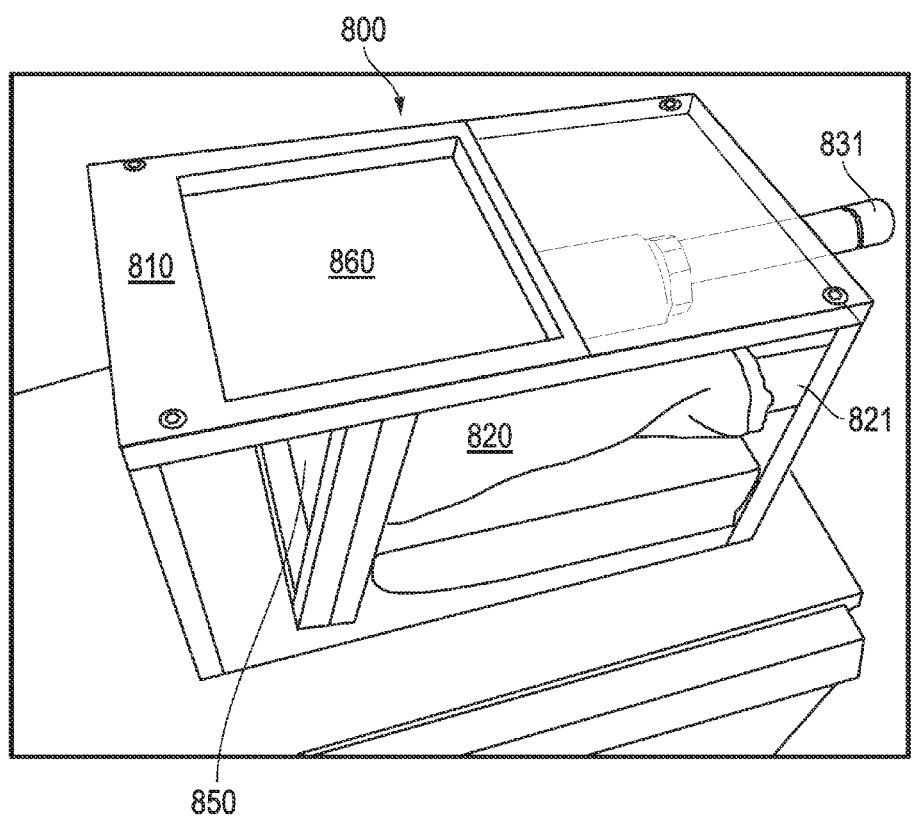
FIGS. 8A and 8B are photographic illustrations of an embodiment of an in vitro model system.
Figure 8B:
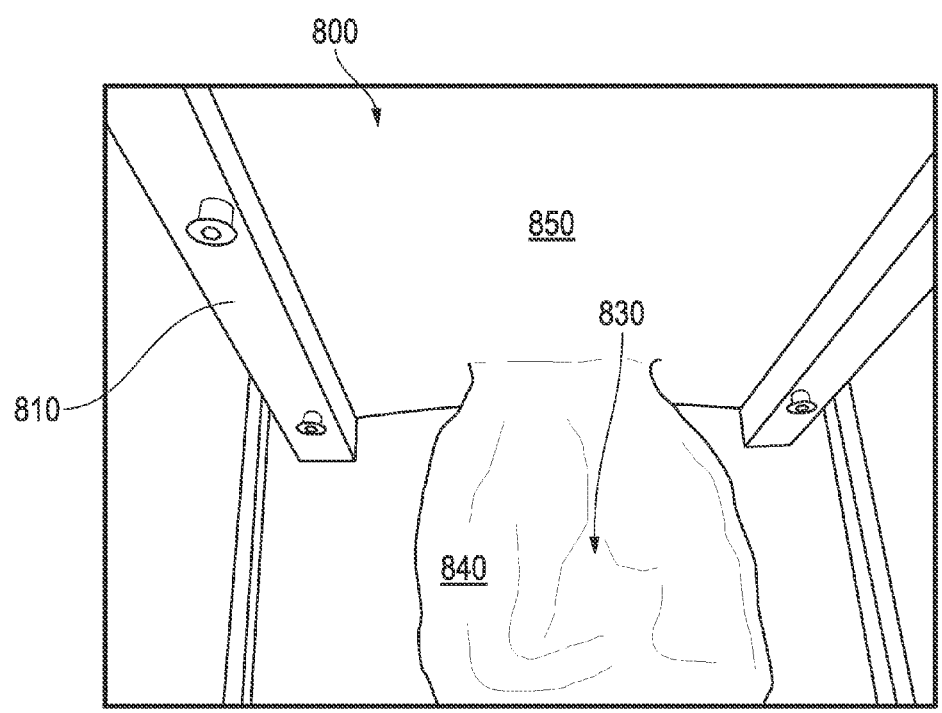

In the non-limiting embodiment of FIG. 1, each in vitro organ is depicted as being sealed, with no fluid connections to any fluid sources. However, it should be appreciated that one or more of the in vitro organs may be fluidly connected to one or more fluid sources. The fluid sources may be located within the thoracic cavity, or alternatively, external to the thoracic cavity. For example, FIGS. 8A and 8B depict an example embodiment in which the lungs 820 and heart 830 are configured to be fluidly connected to a fluid source disposed outside the thoracic cavity via tubes 821 and 831, respectively.

Figure 2:
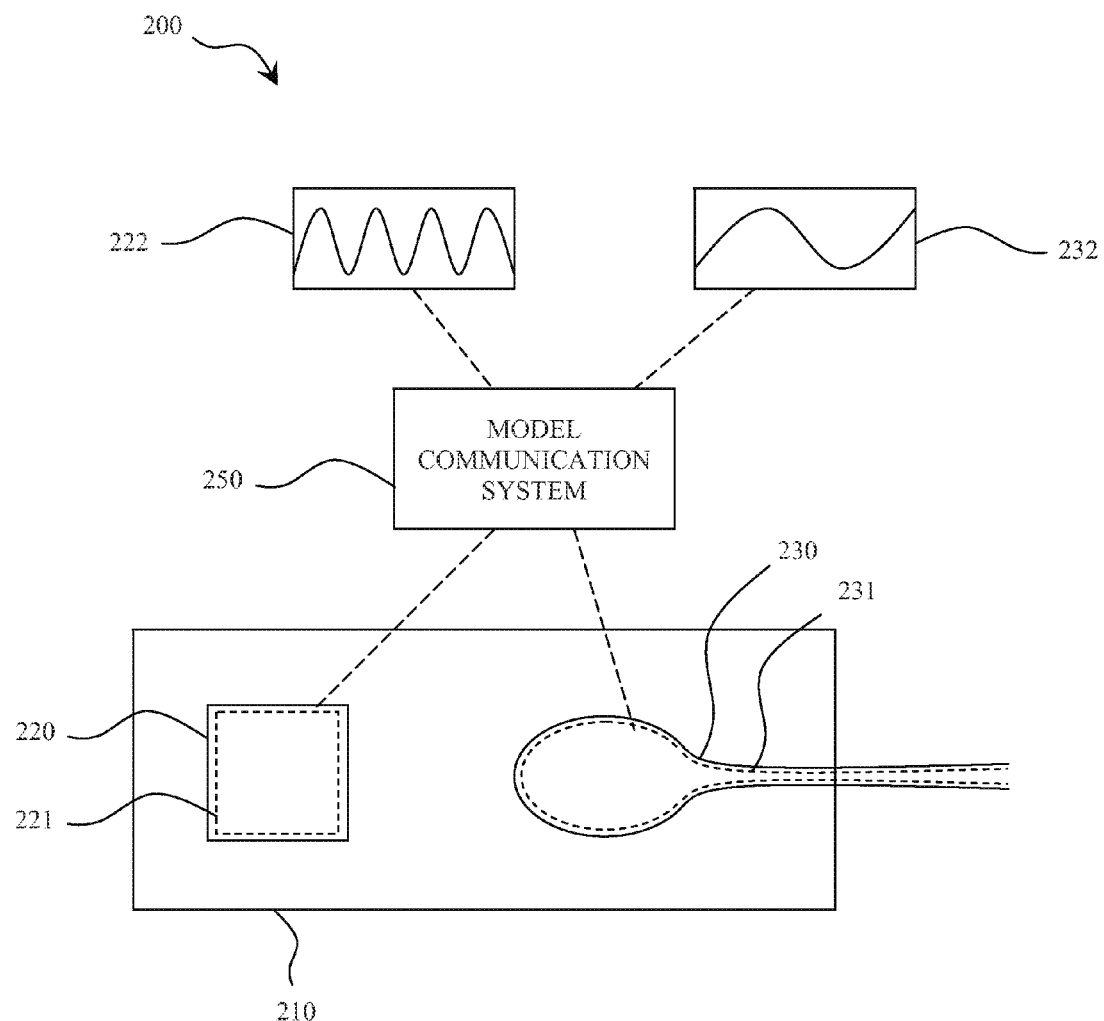
FIG. 2 is a schematic view of an embodiment of an in vitro model system comprising a model communication system for communicating at least one pressure-frequency profile to at least one anatomical component.

FIG. 2 shows a schematic of an embodiment of the invention comprising an in vitro model system 200. In this non-limiting example, the model system 200 comprises anatomical components 210, 220 and 230. Anatomical components 220 and 230 are disposed and partially disposed within anatomical component 210, respectively. Components 220 and 230 are also configured to contain fluids 221 and 231, respectively. Component 220 is depicted as being sealed, whereas component 230 is not sealed and may be connected to a fluid source. However, it should be appreciated that embodiments of the present invention could encompass any number of anatomical components, and collectively configured to contain least one fluid. Anatomical components may be but need not be, for example, disposed within, partially disposed within, configured to surround, or configured to partially surround other anatomical components. Any of the anatomical components that contain a fluid may be, for example, sealed, partially sealed, fluidly connected to other anatomical components, and/or fluidly connected to fluid sources.

The embodiment of FIG. 2 further comprises at least one pressure-frequency profile. FIG. 2 depicts, for example, two distinct pressure-frequency profiles, 222 and 232. However, it should be appreciated that embodiments of the present invention may comprise more or less than two pressure-frequency profiles. The number of distinct pressure-frequency profiles may be, for example, greater than, equal to, or less than the number of anatomical components and/or fluids.

The embodiment of FIG. 2 further comprises a model communication system 250 for providing at least a component of the at least one pressure frequency profile 222, 232 to the at least one fluid 221, 231. The model communication system may, for example, communicate the sum of pressure-frequency profile 222 and a damped component of pressure-frequency profile 232 to the fluid 221 of anatomical component 220, but communicate nothing directly to the fluid 231 of anatomical component 230. It should be appreciated that many communication combinations are possible for a given set of anatomical components and pressure-frequency profiles. For example, in another non-limiting embodiment, the model communication system could communicate a component of pressure-frequency profile 232 to fluid 221, and communicate the sum of pressure-frequency profiles 222 and 232 to fluid 231. Moreover, figures throughout this disclosure serve merely as an example of exemplary embodiments of the system and components, and the specific depictions, contours and dimensions herein do not serve as limitations; these components may be implemented in a number of different ways.

Generally speaking, the function of the model communication system is to regulate the pressure of the fluid or fluids inside the various anatomical components. It should be appreciated that the fluid pressure can be regulated in a number of ways, and that the model communication system can thus take various forms. The only limiting characteristic of the model communication system is that it provides at least a component of at least one pressure-frequency profile to at least one fluid. The model communication system may communicate with the fluid by, for example, pumping the fluid. It should be understood that communication lines between the model communication system and other components, as well as communication lines among internal components of the model communication system itself, may be electrical (either hardwired or wireless), mechanical, magnetic, electromagnetic, electromechanical, or any combination thereof. It should also be appreciated that the various devices, systems, components and modules discussed herein can also be adapted to be visible on a medical imaging modality, such as at least one of magnetic resonance imaging, computed tomography, fluoroscopy, or other radiological modalities.

In one non-limiting embodiment, the model communication system may comprise, for example, a controller, a motor, an actuator, and a pumping that is fluidly connected to at least one anatomical fluid. The controller may be, for example, a digital computer, microcontroller, microprocessor, or other computationally-based means for regulating the behavior and performance of the model system. The controller may be configured to receive data representing the at least one pressure-frequency profile. The controller may further be configured to be in communication with the motor. For example, the controller may be configured to communicate to the motor any one or more of the following: one or more pressure-frequency profiles, a damped or un-damped component of a pressure-frequency profile, a scaled or un-scaled component of a pressure-frequency profile, and/or any sum or combination thereof. The motor may be, for example, an AC or DC electric motor, a stepper motor, or a gear motor. The motor may be configured to, for example, convert the signal from the controller into kinetic motion and communicate this motion to the actuator, such as, for example, a rotational or linear actuator. In turn, the actuator may be configured to, for example, communicate motion from the motor to the pumping mechanism. The pumping mechanism may be, for example, a bellows pipette, a metering pump, a peristalitic pump, or a piston-based pumping mechanism fluidly connected to an anatomical fluid. For example, the pumping mechanism may be configured to pump fluid within a fluid source that is connected via a tube to an aperture in an anatomical component. This embodiment is merely one non-limiting example of how the model communication system may regulate the pressure of an anatomical fluid.

Figure 18:
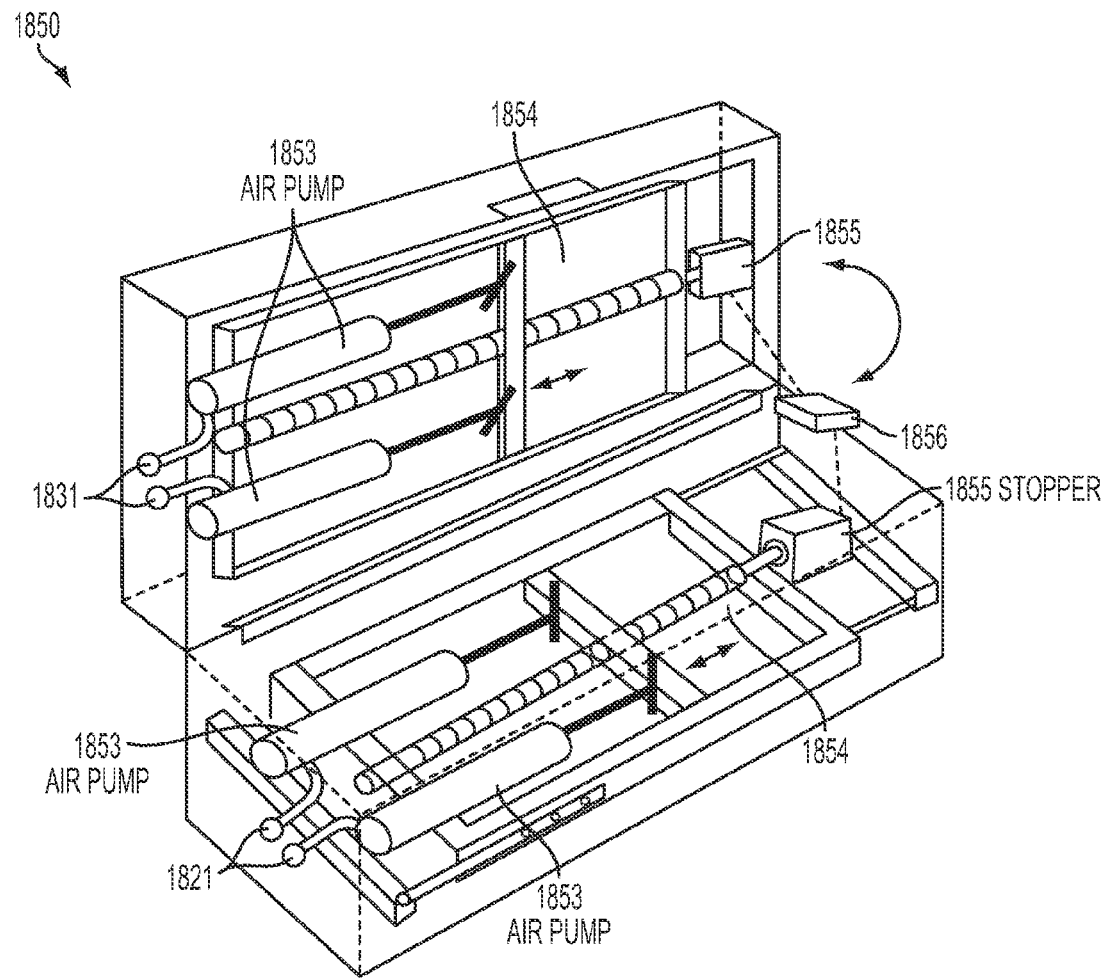
FIG. 18 is a schematic perspective view of an embodiment of a model control system.

FIG. 18 provides a non-limiting example of such a model communication system 1850. A controller 1856 is configured to communicate data signals representing pressure-frequency profiles to the two stepper motors 1855. In turn, the motors convey the pressure frequency profile to the actuators 1854. Each actuator drives a pair of air pumps 1853. The two sets of air pumps may be configured to be in fluid contact with an anatomical fluid or external fluid source via fluid connection tubes 1821 and 1831. For example, tubes 1821 and 1831 may be fluidly coupled to a lung fluid source and a cardiac fluid source, respectively.

Figure 3:
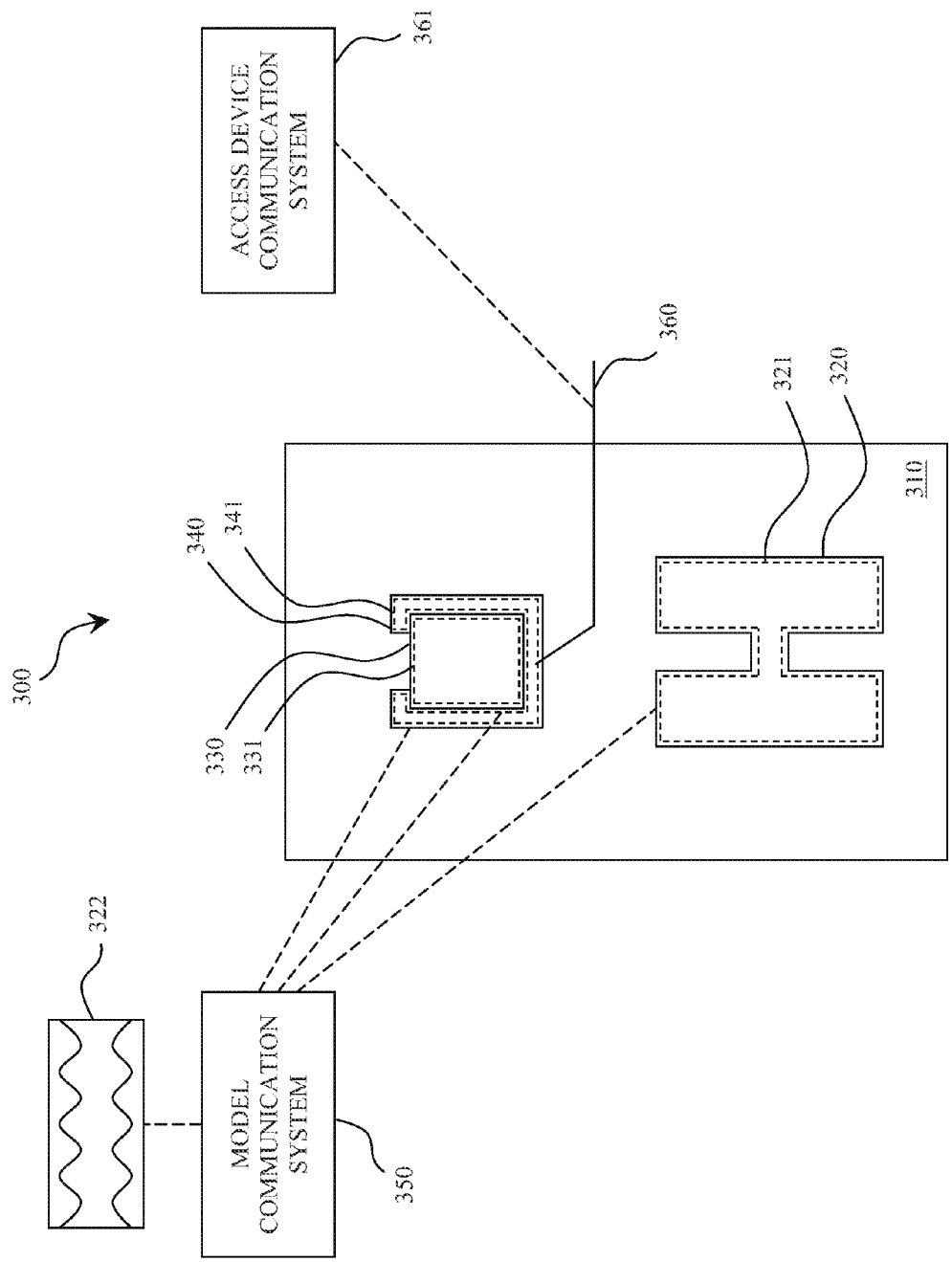
FIG. 3 is a schematic view of an embodiment of an in vitro model system further comprising an access device and access device communication system.

FIG. 3 shows a schematic of another non-limiting embodiment of the present invention comprising an in vitro model system 300. The model comprises the following anatomical components: a thoracic cavity 310, lungs 320, a heart 330, and a pericardium 340. The lungs, heart and pericardium are configured to contain a lung fluid 321, a cardiac fluid 331, and a pericardial fluid 341, respectively. The model system further comprises a model communication system 351. The model communication system 350 may be configured to communicate at least a component of at least one pressure-frequency waveform 322 to at least one of the lung fluid 321, the cardiac fluid 331, and/or the pericardial fluid 341.

The embodiment of FIG. 3 further comprises an access device 360 and an access device communication system 361. The access device may be, for example, any one or more of the following: a surgical instrument, a needle, a probe, a catheter, or a minimally invasive device. For example, the access device 360 may be configured to sense a pressure profile, a frequency profile, or a pressure-frequency profile. The access device may be, for example, a device of the type described in one or more of the following references to Mahapatra et al.: PCT/US2008/056643, PCT/US2008/056816, PCT/US2008/057626, and PCT/US2008/082835. An aspect of an embodiment of the present invention provides a system for the access device that can serve as a guide way for introducing other devices into the pericardium, for instance sheath-catheters that might subsequently be employed for procedures in the pericardium and the epicardium of the heart. Other devices that the present invention device may accommodate include, but not limited thereto, the following: ablation catheters, guidewires, pacing leads, pacing catheters, pacemakers, visualization and recording devices, drugs, lumens, steering devices or systems, drug or cell delivery catheters, fiber endoscopes, suctioning devices, irrigation devices, electrode catheters, needles, optical fiber sensors, sources of illumination, vital signs sensors, and the like Theses devices may be developed for procedures in an integral body part or space.

In an aspect of an embodiment, the pressure, frequency, or pressure-frequency profile sensed by the access device may be communicated to a user via an access device communication system. For example, the access device communication system 361 may be configured to receive a signal from the access device 360, and communicate information to the user via an audio and/or visual display. It should be appreciated that the pressure related readings and data may be received by the user, clinician, physician, or technician or the like by visual graphics, audible signals (such as voice or tones, for example) or any combination thereof. Additionally, the pressure related readings and data may be reduced to hard copy (e.g., paper) or computer storage medium. It should be appreciated that the pressure related readings and data may be transmitted not only locally, but remotely as well.

The information communicated to the user may include, for example, the pressure profile or pressure frequency profile itself. An example of such an access device communication system can be seen in FIG. 6. Specifically, the access device communication computer 650 may be configured to display pressure-frequency waveforms as shown. Another example communication from an access device can be seen in FIG. 24. In this example, the tip of an access device has passed through four distinct anatomical regions of an in vitro model system, each region with its own unique pressure-frequency profile.

Figure 24:
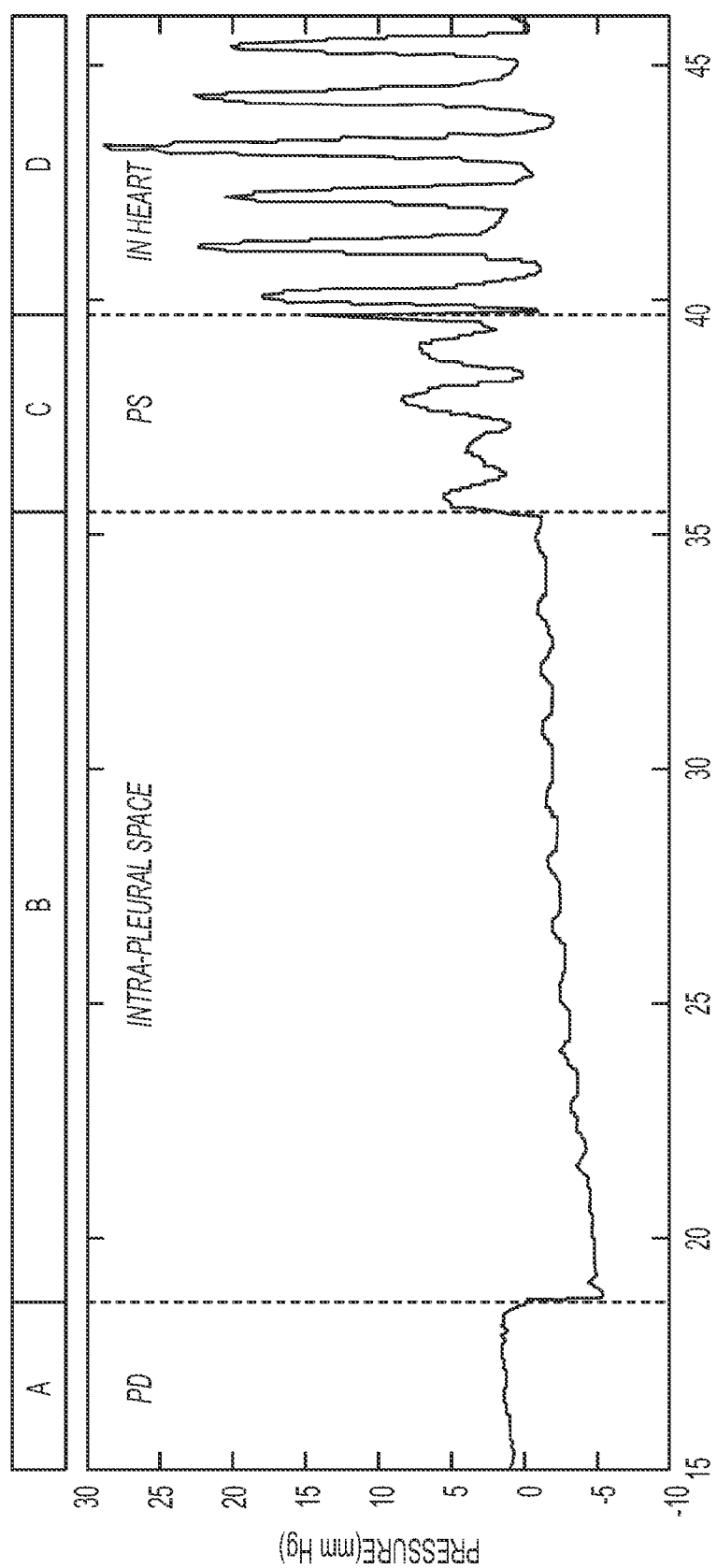
FIG. 24 is a graphical representation of pressure versus time, as observed by an embodiment of an access device used during a simulated procedure.

In the example of FIG. 24, these regions correspond to atmospheric pressure (PD), an intra-pleural space, a pericardial sac, and the interior of a heart. Additionally or alternatively, the information communicated to the user may also include not only a pressure-frequency profile, but also the actual location of a portion of the access device relative to one or more of the various anatomical components of the model system. For example, the access device and/or access device communication system may be configured to recognize the present location of the tip of the access device based on changes in the observed pressure-frequency profile. Thus, in this example, the access device communication system is capable of communicating to the user whether the tip of the access device is presently located, e.g., in the thoracic cavity, in the pericardial sac, in the heart, etc.

The embodiment of FIG. 3 depicts one way in which the present invention may be configured to test an access device or train a user of an access device. The figure schematically depicts an access device penetrating the thoracic cavity and pericardium in order to access the pericardial fluid. If the pressure-frequency profiles of the various in vitro anatomical fluids are known to have certain distinct properties, or properties that fall within certain ranges, then the process of inserting the access device into one or more of the anatomical components can be used to calibrate the pressure-sensing features of the access device. In a similar manner, the user can implement the process of inserting the access device into one or more of the anatomical components in order to simulate an in vivo procedure. For example, sub-xyphoid pericardial ablation of a human heart can be simulated in part by inserting the tip of the access device through the model's thoracic cavity and further into the pericardium. In this example, the access device communication system can communicate the location of the access device to the user as described above, thereby training the user on how to perform a similar in vivo procedure. Examples of using an access device and/or access device communication system to test an access device or train a user of an access device can also be seen, for example, in FIGS. 5 and 7B.

Figure 5:
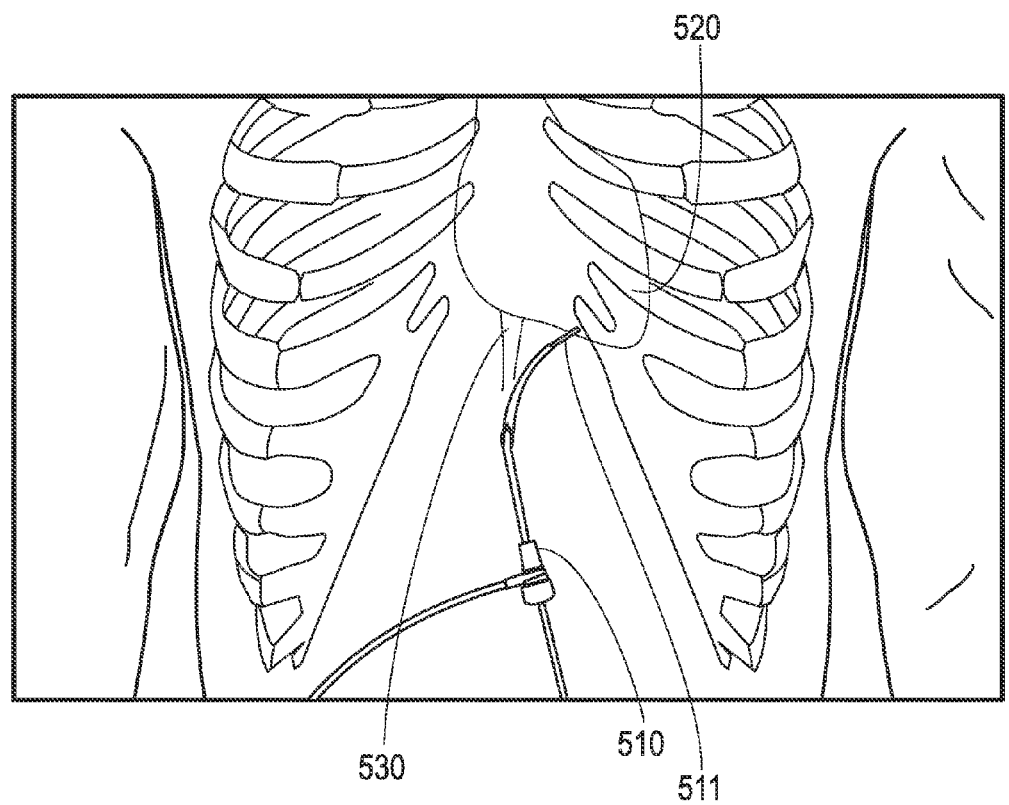
FIG. 5 is a computer-aided illustration depicting an embodiment of an access device that provides sub-xyphoid pericardial access to a heart.

FIG. 5 is a computer-aided illustration depicting an embodiment of an access device that provides sub-xyphoid pericardial access to a heart, including a heart 520, pericardial space 530, and access device 510 with tube 511.

Figure 4:
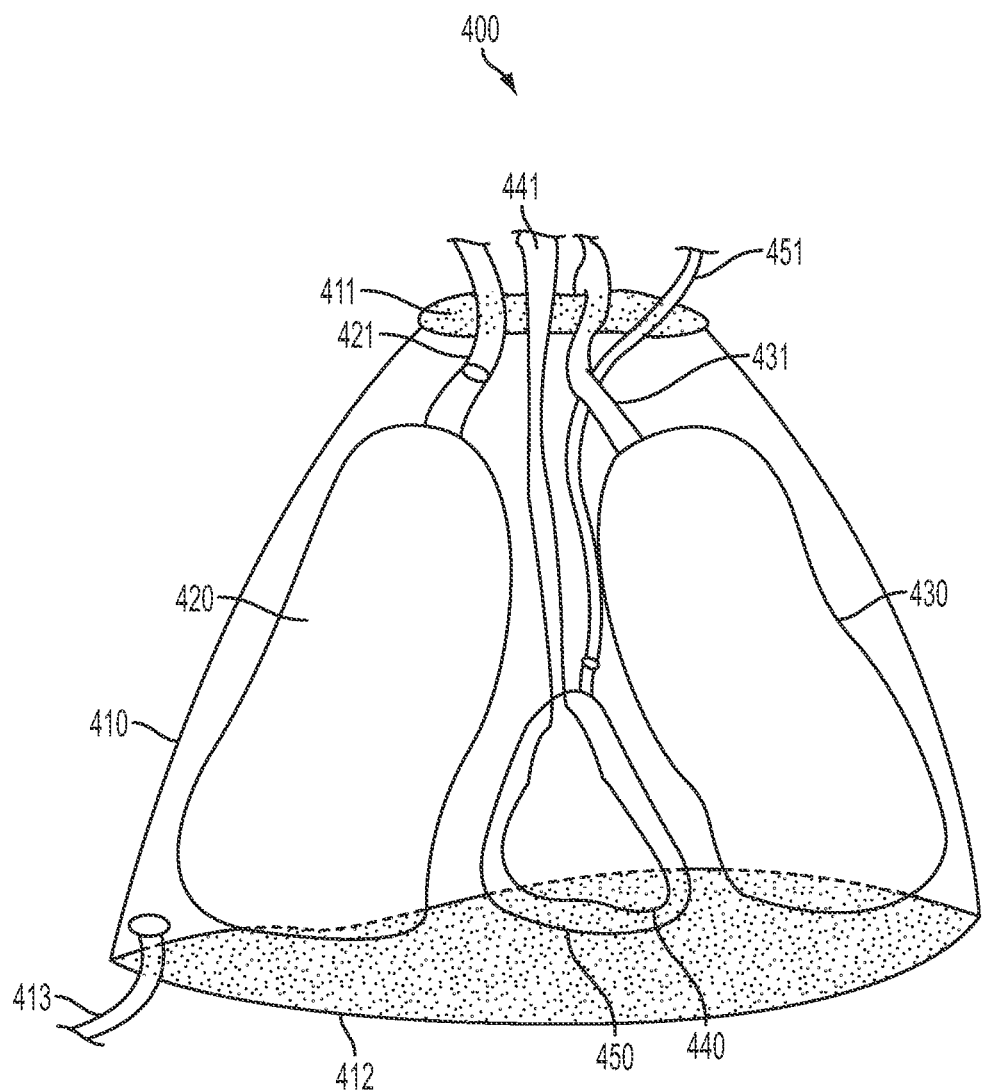
FIG. 4 is a schematic view of an embodiment of an in vitro model system.

FIG. 4 shows a schematic of another non-limiting embodiment of the present invention comprising an in vitro model system 400. In this embodiment, the model comprises anatomical components including a thoracic cavity 410, lungs 420 and 430, a heart 440, and a pericardium 450. The thoracic cavity 410 is sealed from the atmosphere at both ends 411 and 412, and may thus be configured to contain a thoracic cavity fluid. The thoracic cavity fluid may be supplied by an outside fluid source via a tube 413. Anatomical fluids may also be supplied from one or more outside fluid sources to the two lungs, heart and pericardium via tubes 421, 431, 441, and 451 respectively. These tubes may be configured to extend through a surface of the thoracic cavity without breaking the seal of the cavity. Furthermore, the pericardium 450 may be configured to substantially surround the heart 440, as shown. In this manner, the pericardium may be configured to contain a pericardial fluid between the pericardium and the heart.

In the embodiment of FIG. 4, the lungs 420 and 430 are not fluidly connected to one another. This arrangement is in contrast to the embodiment of FIG. 1, in which lungs 120 are fluidly connected to one another. It should be appreciated that the present invention encompasses embodiments in which organs may or may not be in fluid contact with one another. Organs that may be in fluid contact can include but are not necessarily limited to the lungs.

EXAMPLES

Practice of an aspect of an embodiment (or embodiments) of the invention will be still more fully understood from the following examples and experimental results, which are presented herein for illustration only and should not be construed as limiting the invention in any way.

Example and Experimental Results Set No. 1

The First Prototype

Figure 6:
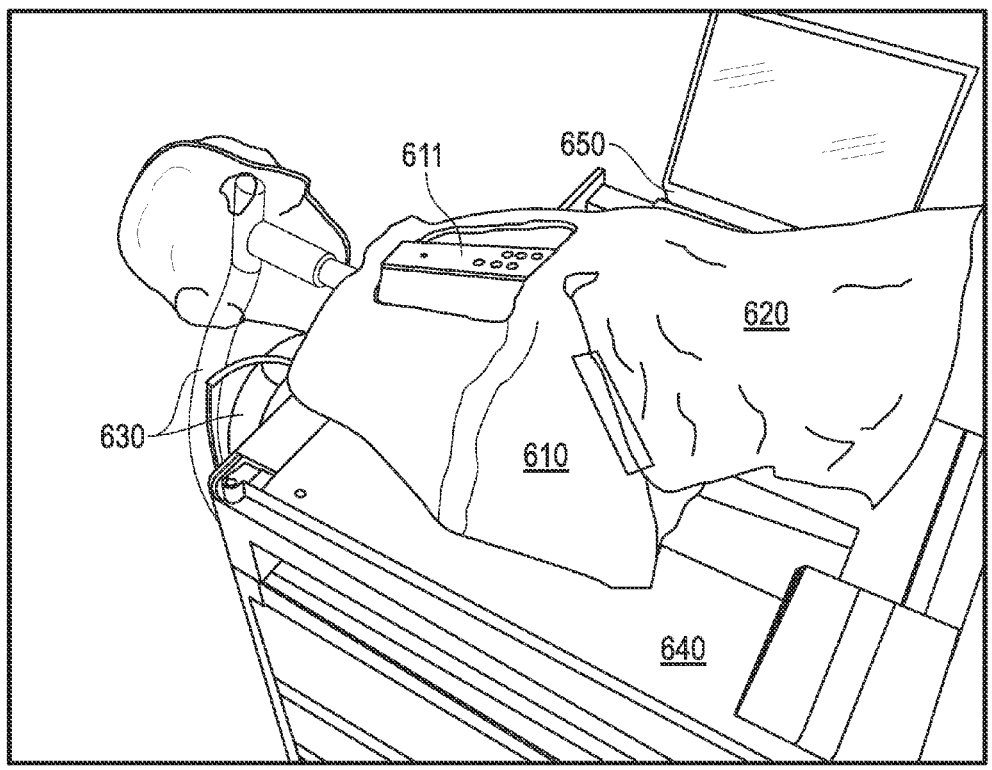
FIG. 6 is a photographic depiction of an embodiment of an in vitro model system.

FIG. 6 shows a bench-top example embodiment of an in vitro model system. The example model system comprises a thoracic section 610 (including a sternum 611), a sub-xyphoid access site 620, lung and cardiac fluid tubes 630, a model communication system cart 640, and an access device communication system, including a computer 650. This embodiment was designed to the scale of the adult human chest, and incorporated two molded balloons that served as air-inflated lungs, and a molded water-pumped heart. The lungs were pumped by a stepper motor-driven bellows, so that the breathing rate and type of inhalation waveforms used in cardiac anesthesiology could be mimicked. In this exploratory version of the system, the heart pump was driven at a constant rate of one beat per minute by a high-torque gear motor. The heart was surrounded by a thin-walled rubber balloon to simulate the pericardial sac, and the thin gap between the outer wall of the heart mold and the inner surface of the pericardial balloon was filled with water. Access procedures could be practiced by passing a pressure-sensing needle through the latex "skin" of the mannequin's sub-xyphoid region 620, then through a layer of molded rubber that served as a surrogate for the diaphragm, and finally into the pericardium. The chest cavity was sealed and the thoracic pressure was monitored by a strain gauge sensor. A laboratory computer 650 was used to acquire the thoracic pressures and the pressure-frequency signals in the access needle. The inspiration and expiration of the lungs not only mimicked the intubated state of an anesthetized patient, but also replicated the lifting force applied to the heart during the breathing cycle. This system allowed us to demonstrate the feasibility of assembling and operating an in vitro model system, to the point where we were able to generate pressure-frequency signals in the surrogate pericardial space that were similar to those found in the human body. Through extensive testing, we clarified a number of design and performance parameters.

Example and Experimental Results Set No. 2

A Second Prototype

Figure 7A:
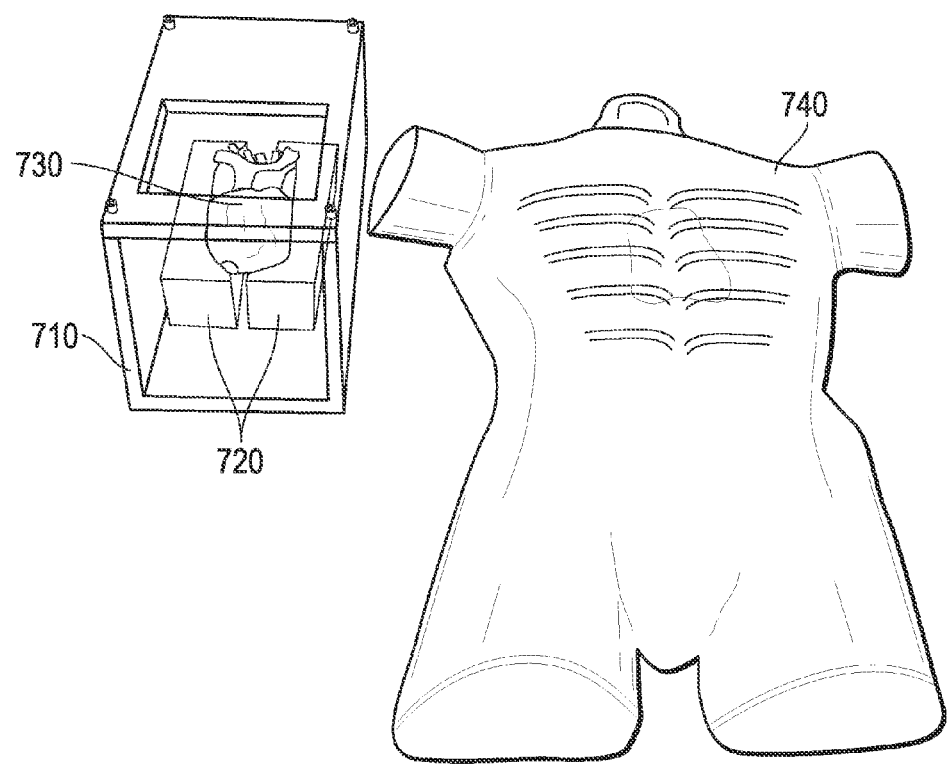
FIGS. 7A and 7B are photographic illustrations of an embodiment of an in vitro model system.

FIG. 7A shows an exploded view of the central features of a second example embodiment of an in vitro model system. The model system comprises a thoracic cavity 710, lungs 720, a heart 730, and a mannequin shell representing a patient's skin 740. In an actual training exercise, the overlying mannequin would be covered with a surgical drape to simulate the patient's situation in the electrophysiology (EP) lab. As a result, the model chest and most of its internal components need only be anthropomorphic in function and not necessarily in form. In practice, this meant that we were able to redesign the chest and its Contents and make everything more modular for ease of assembly and use. In this example embodiment, the thoracic cavity was a Lucite® chest box that served to hold the two latex-molded lungs. The relaxed-state volume of the molded heart is 220 cm3, which is about 20% less than the average adult heart volume of 280 cm3. That molded heart is shown for scale relative to the Lucite® mannequin, which could be placed on top of the chest container during use.

Also shown in FIG. 7A, to the right of the mannequin, is a second replica of a heart, created via rapid prototyping from an open-source SolidWorks™ design. This second replica was slightly oversized compared to the one in the chest case. A thin layer of Dragon Skin® silicone rubber was cast on this second model in order to make the pericardium, which was then slipped over the latex-molded heart. The compliance of the resulting pericardial sac allowed for the virtual space between it and the outer wall of the heart to be converted to an actual one by the injection of water to mimic the pericardial fluid. Also shown in FIG. 7A is one of the stepping motors used in the simulator. In this improved version of the system, both the heart and lung pumps were driven by computer-controlled stepping motors. This allowed us to not only simulate any anesthesia waveforms that might be needed, but also to simulate variable heart rates and arrhythmias. Moreover, any given heart or lung pumping profile could thus be easily documented, archived and repeated as necessary for practice purposes. In an interesting change relative to our first system, the lungs were now water pumped and the heart was air pumped, to insure that the correct forces were applied to the surrogate pericardial fluid by the components of this resealed system.

Figure 7B:
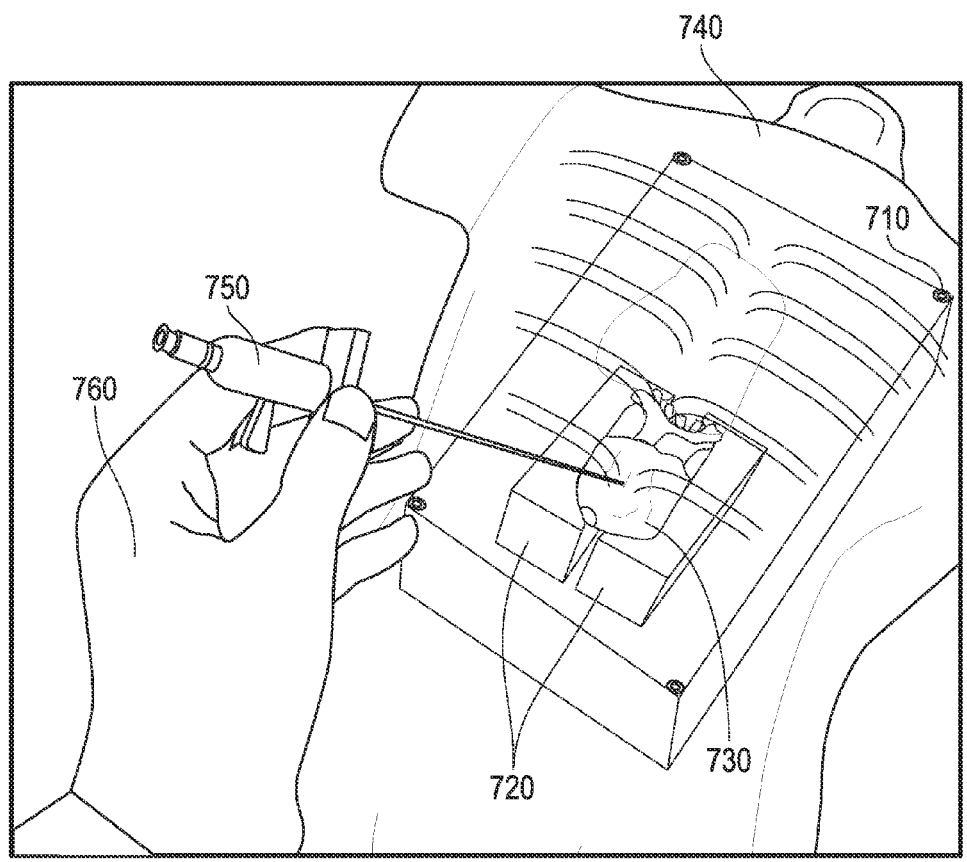

FIG. 7B shows a user 760 holding a representative access device 750 in position above the mannequin. During use of the simulator, data acquisition for the epicardial-access training procedures is handled by a program in LabVIEW® SignalExpress™ (National Instruments, Austin, Tex., US). This program also provided the ability to perform a near-real-time frequency analysis and the display the fast Fourier transform (FFT) of a selected window of data along with the time-domain record of the actual acquired signal. Most typically, the access device consisted of a fiber-optic pressure sensor (FISO, Quebec, Canada) that was positioned within the tip of an 11 cm long, 17 gauge Touhy needle. The output signal from the sensor's pre-amplifier was acquired at a sampling rate of 1 kHz and processed by the data-handling program, with either the raw signal or the FFT presented to the trainee in a user-selectable window on the host computer's display.

FIGS. 8A and 8B show two views of a similar embodiment of an in vitro model system 800. This particular embodiment comprises a thoracic cavity 810, lungs 820, a heart 830 which is at least partially surrounded by a pericardial sac 840. The pericardium 840 is attached to a diaphragm 850, and can be accessed by an access device through a sub-xyphoid access site 860. A 1 cm thick layer of Dragon Skin® silicone rubber functions as the abdominal skin and muscle sheath of the model. Another such layer of the rubber serves as the diaphragm. The two layers are bonded together to form a "T" shape as shown in the figure. Both branches of this "T" are fixed onto the chest box by Lucite® frames, and the joints are made leak free with silicone sealant. The surface area of the sub-xyphoid injection site is large enough to permit a grazing-incidence approach to the right ventricle of the model heart, in imitation of the actual clinical access procedure. Upon inflation, the lungs expand within the chest cavity, thus applying cyclical pressure to the pericardium and diaphragm. As seen in FIG. 8B, the frames holding the diaphragm and sub-xyphoid injection site have been removed from the chest cavity and placed upside down on a table to reveal the internal structures. The interesting things to note are the close, full-organ fit of the pericardial sac to the heart and the attachment of the pericardium to the diaphragm at the apex of the heart. The close fit of the pericardium is meant to provide the trainee with a realistic clinical test, viz., attempting to snag the thin pericardial membrane at grazing incidence (in order to minimize the risk of perforating the heart) with and without pressure-frequency guidance during the training session. By using transparent Lucite® as the construction material for the simulator's chest the trainee can do the procedure with and without visual feedback (i.e., with and without the mannequin draped) in order to practice the procedure more effectively. The attachment of the pericardium to the diaphragm at the apex of the heart provides a key measure of physiological fidelity by helping to hold the heart in place within the chest while the lungs work against it during inhalation, thus insuring that the mock pericardial fluid is hydrodynamically influenced by the pumping of both the heart and the lungs. Perhaps most significantly, since the abdominal muscle sheath, diaphragm and pericardial sac surrogates are thus all bonded together to form one continuous unit, it is easy to conceive of this assembly being made available as a single integrated replacement part from a manufacturer marketing it. This is an important point, since this assembly will eventually require either repair or replacement after a sufficiently large number of practice access procedures have been performed on it.

Several types of validation studies have been carried out with our improved system. In one of them, the stepping motor-driven pumping rates for the heart and lungs were tuned to the vital-function conditions that were present during an institutionally-approved in vivo clinical trial of epicardial access employing a canine model. The results are shown in FIG. 9. The upper trace is the measured, hydrodynamic pericardial pressure in the canine model. Superimposed on the high-amplitude, low-frequency 0.2 Hz) waveform shown there is a low-amplitude, high-frequency component 1 Hz) produced by the heart beat. The hydrodynamic pericardial signal measured in the simulator's mock pericardial fluid (water) under nominally identical conditions is shown in the lower trace. The same periodicities are easily discerned from visual inspection of that waveform, although the amplitude ratios are different for the in vivo and in vitro cases. However, during both studies we noted that the cardiac component of the waveform was not present either before the tip of the access needle had initially entered the pericardium or after it had been withdrawn from the pericardial sac, thus confirming the simulator's ability to credibly represent the clinical situation. Some further details of our design, construction and testing efforts are presented elsewhere.

It would not be unreasonable to introduce a version of the in vitro model system in which the pericardial sac was fixed to the molded heart at several locations. This would replicate the effect of post-surgical adhesions, which in practice reduce the amount of fluid in the pericardial space and thus decrease the strength of the associated pressure-frequency signal. It would also be possible to introduce a motional artifact in the mannequin itself, to mimic the movement of the chest walls during the respiration cycle. Lastly, a significant materials-related improvement would be achieved through the use of a substance that was more fully self-healing than the silicone rubber presently employed for abdominal sheath, diaphragm and pericardial sac. Even when using very small gauge needles in the access device, that assembly eventually develops pericardial fluid leaks that are large enough to require either manual sealing of the penetration holes or replacement of it altogether.

We envision using this system not only as, for example, a training tool for electrophysiologists interested in doing epicardial procedures, but also, for example, as a research tool for testing new epicardial technologies. For instance, the existing endocardial ablation catheters are not properly configured for epicardial use. In particular they have the lengths and curvatures inappropriate for epicardial applications. The simulator could serve as a useful intermediate tool for testing specially designed epicardial ablation catheters and optimizing their construction and performance prior to undertaking costly in vivo trials for clinical commissioning. A similar situation holds for the testing of custom-designed epicardial pacing leads, as well.

Example and Experimental Results Set No. 3

Simulating Arbitrary Dynamic Pressure Waveforms for Anatomical Training and Testing Models In an aspect of an embodiment, a LabVIEW™ virtual instrument controls the software end of the in vitro model system, creating a range of physiological waveforms given numerous input parameters. The application of this simulation is towards pressure guided transthoracic epicardial access for electrophysiology procedures. While reaching the epicardium, the two pressure waveforms encountered are in the thoracic cavity, which mimics the respiratory wave due to local connections to respiratory structures, and in the pericardial cavity, which sums the thoracic wave with a damped heart component due its local connections to both respiratory and cardiac structures. The LabVIEW™ instrument can create and mimic either of these waves, over a range of ideal and non ideal physiological conditions. Five different thoracic waves can be selected, which are arbitrary waveforms that visually mimic the five most commonly used mechanical ventilation curves in the clinic, with flexible options as to their duration, pause, and inspiration to expiration ratio. For pericardial waves, the selected respiratory wave is summed with a heart component, which is a simple sine wave, with options for the heart rate, heart wave amplitude, and amplitude of white noise if non-ideal conditions are preferred. The front panel of the program can be seen in FIG. 10.

The virtual instrument builds the desired thoracic or pericardial electrical waveform at a scale indicated by a group of inputs and displays the thoracic and cardiac components as well as their FFT's, and the summed pericardial waveform. The sampling frequency, or resolution of the wave can be programmed, but reaches an upper limit depending on the length of the curve in the time domain, due to limited memory of the driver, which is being programmed. After assembling the waveform with respect to time, the program takes the difference between each point in time, and recompiles the difference values as a sequence of commands for stepper motor speed and step sizes and sends the compiled program to a stepper motor driver. An input for a scale up factor changes the unit less original waveform, to an expected amplitude of output pressure, and controls the magnitude of each stepper motor movement with respect to time. Due to the variability in the system, the effect of a given scale up factor was characterized experimentally, and is discussed further in the methods and results section.

Figure 11:
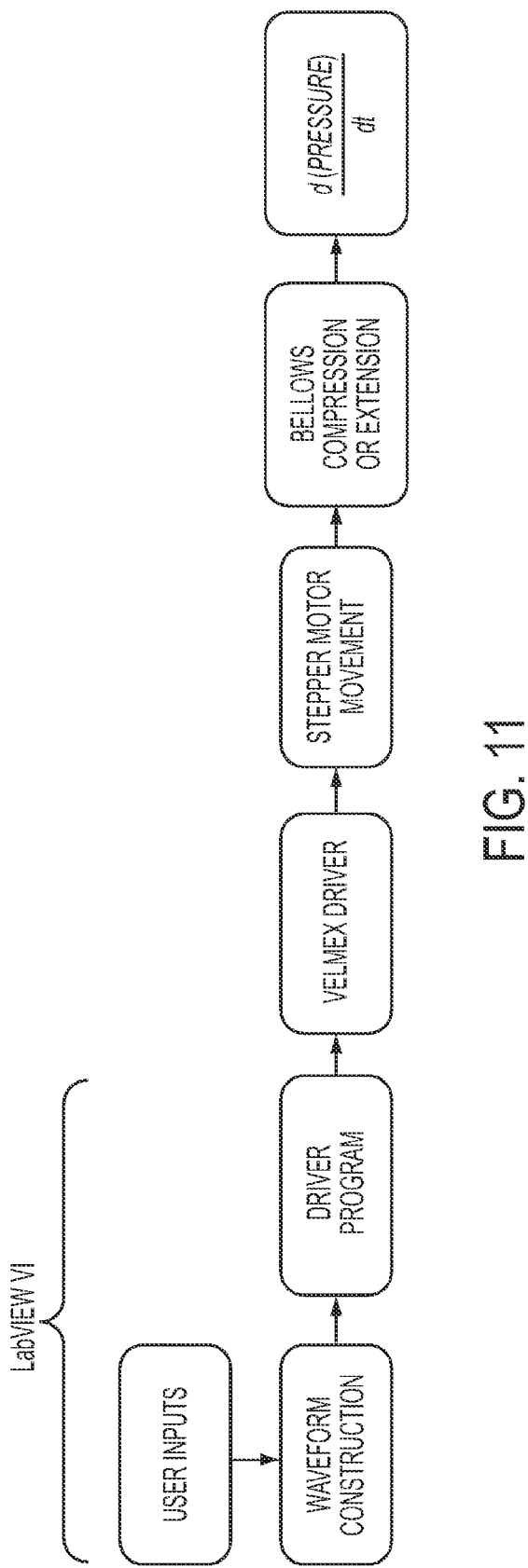
FIG. 11 is a flow diagram of information and corresponding actions in an embodiment of the in vitro model system.

The compiled program from the LabVIEW™ program is sent via RS-232 serial line to a Velmex driver controller, which utilizes a custom programming language to execute stepper motor functions on Velmex brand stepper motors. Following the directions of the program, the driver precisely powers and drives the stepper motor to move the proper number of steps at a given instantaneous speed, twisting the stepper motor clockwise or counterclockwise. The stepper motor is firmly mounted to a linear actuator screw with an attached stage, which moves laterally given a rotational torque from the twisting motor. The final effect is the forward and backward movement of the linear actuator stage in a manner, which mimics the forward and reverse displacement of the original waveform with time. The linear actuator's stage acts on the compliant end of a bellows pipette, which can be connected to any male luer slip device, including insertion sites and pressure transducers. The final result is a sealed pressure chamber, which increases and decreases pressure according to the actuator stage movement, mimicking the pressure fluctuations of a thoracic or pericardial cavity with the characteristics of the original program inputs. The complete flow of information can be seen in FIG. 11.

The performance, robustness, and accuracy of the pressure simulator to recreate a given waveform were assessed by methods of correlation. Two different groups of tests were performed using pressure instrumentation used by researchers in previous work attached to the bellows pipette open end. The first test was a characterization study of the scale up factor, to find the expected multiplier, which relates the amplitude of the unit less reference waveform to the amplitude of the output pressure waveform. For this test, data from the pressure transducer was collected in real time via serial line, sampled at a controlled rate. The second was a correlation test between interpolated sample reference waveforms, and the output waveforms. This tested the ability of the pressure simulator's ability to truly mimic the desired waveform as generated by the researchers' inputs. The second test utilized an analog output option from the pressure sensor, and data was collected at a controlled sampling frequency through a digital storage oscilloscope.

Due to the large number of variables and parameters in the system, as well as given uncertainties in the bellows pipette as a component, it was difficult to characterize the expected amplitude of the output pressure in comparison to the original reference waveform based on an analytical transfer function. Because of this, an empirical method was designed for characterizing a multiplier for the expected amplitude of the output pressure waveform given an input function and scale up factor.

A group of reference sine waveforms with different scale up factors were statistically compared to data acquired from a pressure transducer attached to the bellows chamber. Both the reference waveform and pressure data acquisition occurred at the same sampling rate of 10 Hz, large enough to be greater than the Nyquist frequency of the waveforms, and small enough that a miniscule widening or narrowing of the output waveform in the time domain due to stepper motor imperfections would not cause a discrepancy between the number of points for the two waves, making statistical analysis as simple as possible. Three different sine waves were tested, with center frequencies of 0.5, 1, and 1.5 Hz, all with a peak amplitude of 0.5 (the reference waveform is unit less). Each sine wave was tested multiple times at scale up factors of 50, 100, and 200. The pressure output for each trial was plotted against the reference waveform, and a linear best fit approximation of the two data sets was estimated to find the pressure multiplier given a relatively constant initial pressure near 30 mmHg.

At higher sine wave center frequencies, the change in pressure between each point collected every 0.1 seconds is much higher. Because there was no way to align the starting time for both the stepper motor and data acquisition precisely, some of the acquired pressure waveforms had minor phase shift deviations from the reference waveform. This small phase shift at high center frequencies caused major distortions in data during statistical analysis, so out of the 7 trials for each condition, only the 3 with the highest correlation coefficients were kept for data analysis, because they accurately captured the waveform at a similar phase as the reference waveform. An example of this phase shift can be seen in FIG. 12.

The most important group of tests involved simulating different pericardial waveforms in the pressure chamber and statistically comparing the pressure output to the input waveform. Upon initial construction of the system, all the thoracic waves were tested, as well as a range of pericardial waves, all of which visually mimicked the input waveform, but a quantitative comparison was imperative to characterize the system's actual performance. Three common ventilation curves were selected, each with large heart component amplitude (⅕ that of the thoracic wave), and a small heart component amplitude (1/20 that of the thoracic wave), visually imitating realistic cardiac amplitudes for healthy hearts, and unhealthy hearts with adhesions, respectively. The three ventilation waves included pressure controlled rectangular, flow controlled rectangular, and flow controlled sine waves. Breath duration, inspiration to expiration ratio, and other input parameters were held constant between each waveform to limit the amount of variability in the data collection. All waveforms had a sampling frequency of 20 Hz in the program, to create a very smooth and well defined wave. Each waveform was recreated four times using the exact same compiled waveform program with the actuator stage always at the same initial location, with the pressure in the output chamber monitored by a digital storage scope sampling at 100 Hz. The 100 Hz output waveform was then compared to the linearly interpolated input waveform using the equation for a linear correlation coefficient ($\rho$).

Linear Correlation Coefficient     Equation 1

$$\rho_{x,y} = \frac{Cov(x, y)}{\sigma_x \sigma_y}$$

where $$Cov(x, y) = \frac{1}{n}\sum_{i=1}^{n} [(x_i - \mu_x)(y_i - \mu_y)]$$

For each trial, the slope (pressure multiplier), intercept (initial pressure), and r2 value (coefficient of determination) were calculated using a linear best-fit trend line of the data. The average slope was calculated for each scale up factor multiplied by the peak amplitude of the reference waveform, further which will be referred to as 'peak scale', with the peak amplitude of the reference waveforms constant at 0.5 for all trials. The average slope approximated the multiple which related the amplitude between the input reference waveform, and the output pressure waveform, given a constant initial pressure near 30 mmHg. For the peak scales of 25, 50, and 100, the average multipliers observed were 2.885±0.057, 5.631±0.107, and 11.347±0.122 mmHg respectively. These three values were placed on a plot comparing peak scale to pressure multiplier, and the resulting linear relationship indicated that the pressure multiplier is equal to 0.133·(peak scale)+(0.0272). Using this formula, the researcher can then predict the pressure scale they can expect to see given the peak amplitude and scale up factor of the input waveform.

Six waveforms were tested for performance of the pressure simulator. The waveforms were all pericardial simulations of pressure controlled rectangular (waves 1 and 2), flow controlled sine (waves 3 and 4), and flow controlled rectangular (waves 5 and 6) ventilation waveforms each summed with either high or low cardiac amplitude components, respectively. Each waveform was run through the simulator four separate times for four sets of acquired pressure data. The output pressure read by the pressure instrumentation was acquired at 100 Hz, and statistically compared to the interpolated input waveform as seen in Equation 1, to assess the linearity between the two data sets. It is important to note that the pressure waveforms are at higher scales than physiological levels, but if incorporated into a larger pressure chamber, more miniscule pressures can be reproduced. However, the waveform itself and the dynamic capabilities of the simulator are the important aspects of this test. Upgrades to the pressure simulator will be discussed in the following section. Correlation coefficients for each of the waveform types can be seen in FIG. 13.

Figure 14:
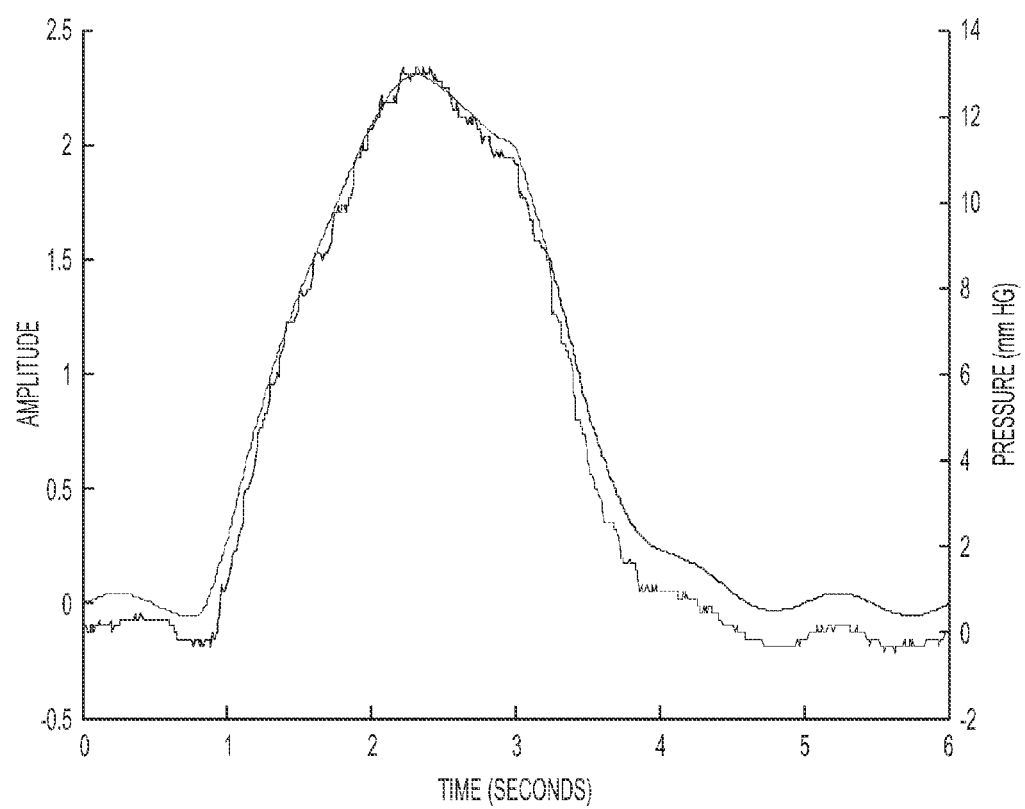
FIG. 14 is a graphical representation of an input reference waveform and an output pressure waveform corresponding to a trial run of an embodiment of an in vitro model system.
Figure 15:
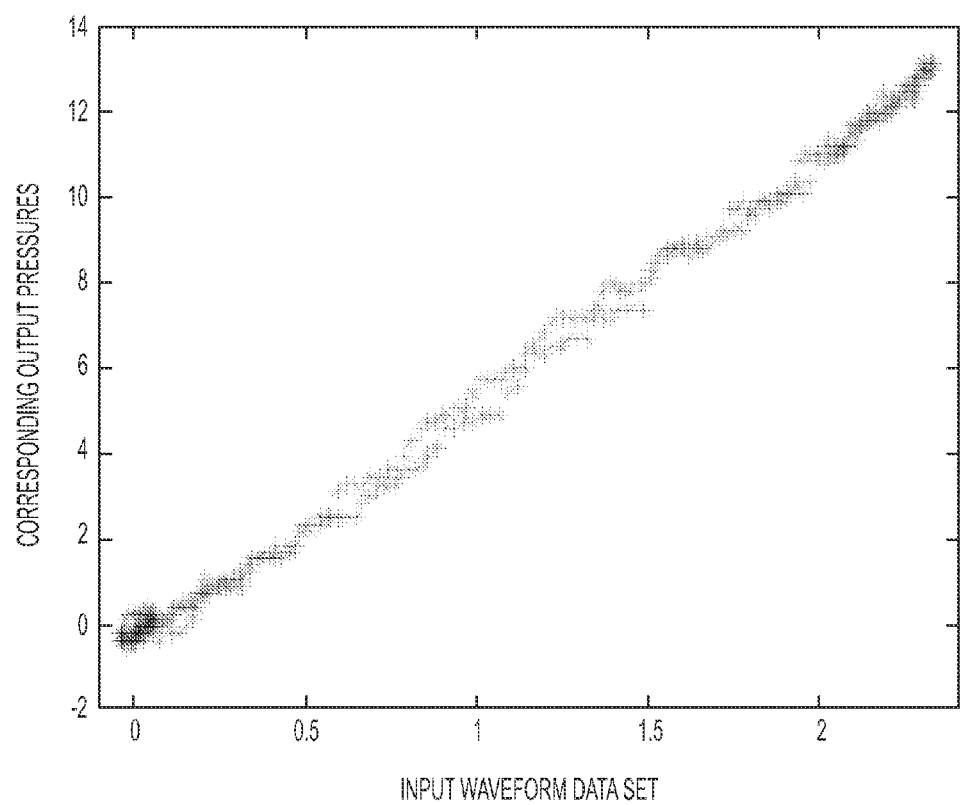
FIG. 15 is a graphical representation of linear trend mapping of the input waveform data set with the corresponding output pressure waveform for a trial run of an embodiment of an in vitro model system.

The average correlation coefficient for the entire data set is 0.9914±0.0058. This shows a very strong linear correlation between all of the output pressure waveforms with the input reference waveforms, which they are intended to duplicate. To further justify the results seen above, an example trial with very strong results is shown in FIGS. 14 and 15. In FIG. 14, the time domain input waveform (smoother line) is graphed alongside the output pressure waveform (rougher line), each on their own individual amplitude scale for Wave 4 (flow controlled sine ventilation wave, low cardiac component), Run 4. FIG. 15 shows the correlation graph between these two data sets, visually identifying the linear relationship between the two.

The ability to mimic realistic pressure waves from sealed human cavities is a useful practice for testing instrumentation and real time signal processing algorithms, but is also important to be able to develop cost effective anatomical training and testing tools for using such devices in an in vitro scenario. The previous results have demonstrated the ability of this low cost system to create chambers with fluctuating dynamic pressures which can be translated to a multitude of applications. Most importantly for the specific field of epicardial electrophysiology, this concept can be applied to anatomical structures to create in vitro human pressure cavities and can be applied for testing pressure guided epicardial access instrumentation, and more importantly, for training clinicians in this new procedure in a safe manner. In a broader sense, this system can be applied to a range of testing scenarios not only in epicardial electrophysiology, but any field which uses real time pressure signal monitoring and processing. While looking into the capabilities of such a system, it is important to note where improvements can be made to create such anatomical models. For example, the low volume bellows pipette can be replaced with a range of different devices including pumps and pistons, which can control larger amounts of pressurized water or air more precisely, given a stepper motor with high enough torque generation, creating larger and more precisely controlled dynamic chambers. As applied to anatomical models, instead of mathematically creating a pericardial wave by summing thoracic and cardiac waveforms, the separate waveforms could be created in the appropriate anatomical structures and see the pneumatic overlap of the pressure waves on the anatomical pericardial structure, as it occurs in the body.

Example and Experimental Results Set No. 2

Figure 16A:
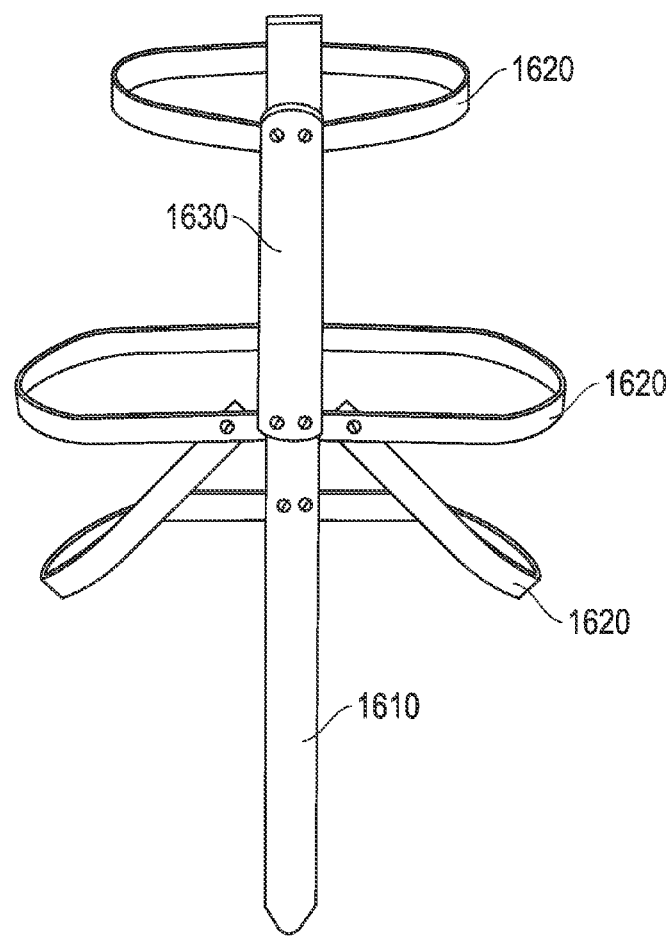
FIG. 16A depicts an aluminum frame of the model thorax.
Figure 16B:
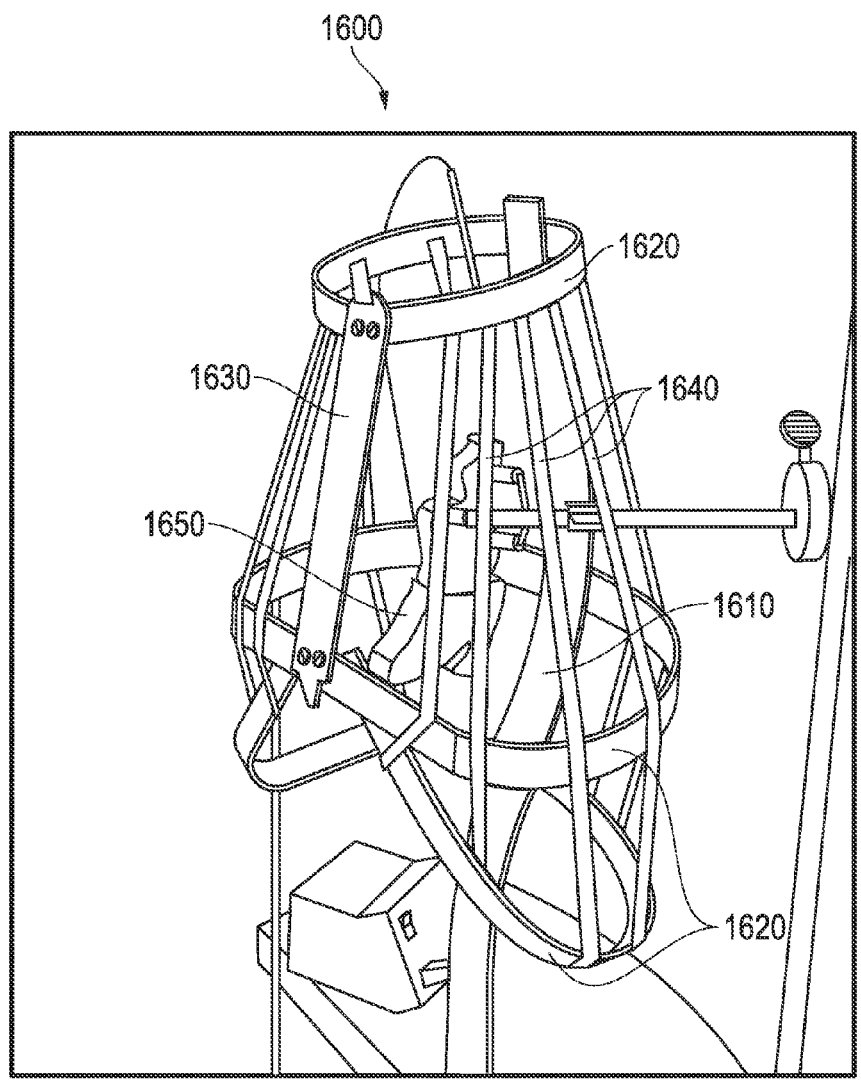
FIG. 16B depicts rubber bands connected to the aluminum frame, and the position of a heart in the model.
Figure 16C:
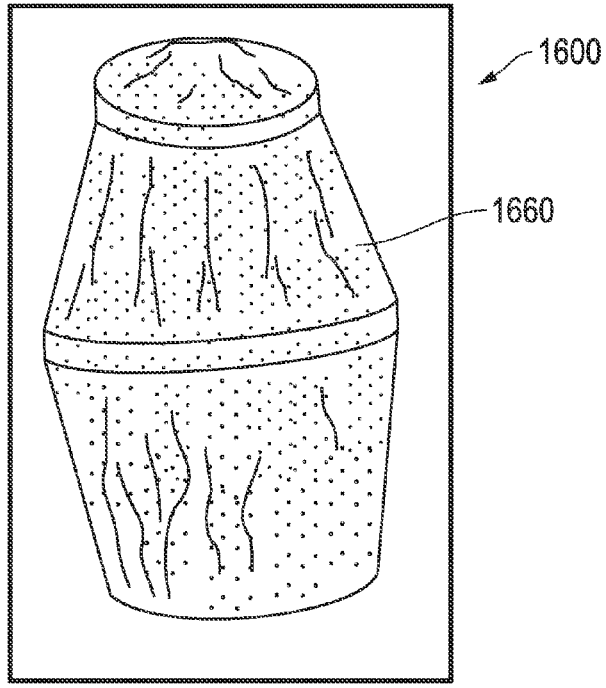
FIG. 16D depicts an aluminum wrap and FIG. 16C depicts initial layers of an outer latex covering applied to the frame.
Figure 16D:
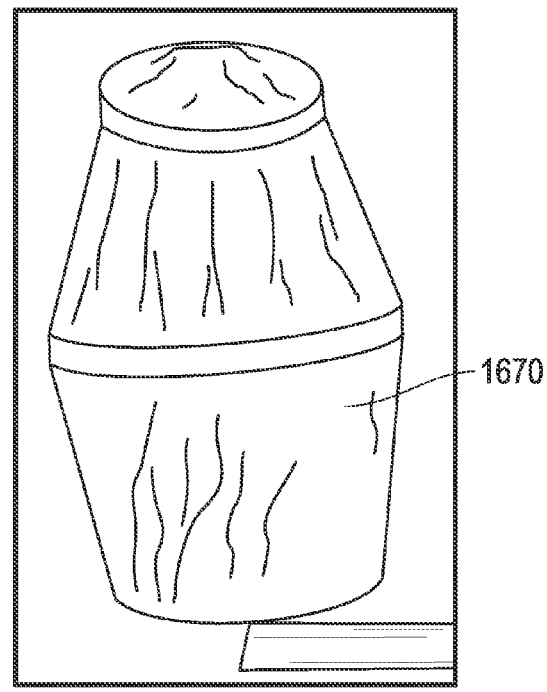

Electro-Mechanical/Pneumatic Device and Method of Use for Simulating Sub-xyphoid Access for Epicardial Electrophysiology Procedures FIG. 16A depicts an aluminum frame 1600 of the model thorax including curved frame members 1620 and connecting members 1610, 1630. FIG. 16B depicts rubber bands 1640 connected to the aluminum frame 1600, and the position of a heart 1650 in the model. FIG. 16D depicts an aluminum wrap 1660 and FIG. 16C depicts initial layers of an outer latex 1670 covering applied to the frame.

In an aspect of an embodiment, a basic shape needed to be established within which the pressure simulations could be performed. Much consideration was given to possible choices ranging from a large plastic bottle, a large balloon, to a geometric representation of the thoracic cavity. Ultimately, it was chosen to create an anatomically accurate frame on which the enclosure can be simulated (FIG. 16A). As the pressure characteristics in the pericardium will be influenced indirectly by the volume of the proximate lungs as well as the volume of the heart, we sought to come as close as possible to replicating the real human geometries. The thoracic cage was first to be constructed to replicate the dimensions of an average thorax. Aluminum rods (1 inch width) will comprise the sternum and the general shape of the spine. Using half inch aluminum rods vertebras 1, 6, and 10 will complete the general shape of the thoracic cage. Over the metallic frame, 3 to 5 layers of liquid latex (room temperature galvanizing from TapPlastics) is applied. Using strong rubber bands, the vertebra will be connected, encapsulating the thoracic cavity. Using a sheet of aluminum to encircle the thoracic cavity, up to 20 coats of liquid latex will be applied. The aluminum foil will be removed and the thoracic mold dried latex will be slid into its intended position over the ribs. A rectangle about 4 inches in width and 6 inches in length will be cut from the latex shell centered on the sternum. A clear Plexiglas with the same dimensions is glued over the cut out. An additional 10 coats of liquid latex will seal the Plexiglas edges so that an air tight perimeter is established. A plastic heart model will be used as the mold for the creation of a heart using liquid latex. In the same way, the lungs are created with their appropriate shape using liquid latex and appropriately sized lung molds. Both the lungs and the heart are hollow and will have a single opening. The two lung balloons will be connected by a ridged tube representing the trachea, which will exit the cavity. Also, another ridged tube will be connected to the heart balloon and will exit the cavity. The heart latex balloon is enclosed by another balloon. This one however, does not have an access and its opening on the top will be tightly sealed. The heart balloon is filled with liquid connected via its exit hose to a liquid holding chamber. The diaphragm and a circular enclosure around the first vertebra will seal the thoracic cage in an air tight compartment. For certain details of construction, see FIG. 16B. After installing the plastic clear window under the sternum, the cage was enclosed and several layers of liquid latex applied (FIG. 16C). The process of creating the exterior covering of the model provides a suitable skin-like surface for it.

Figure 17:
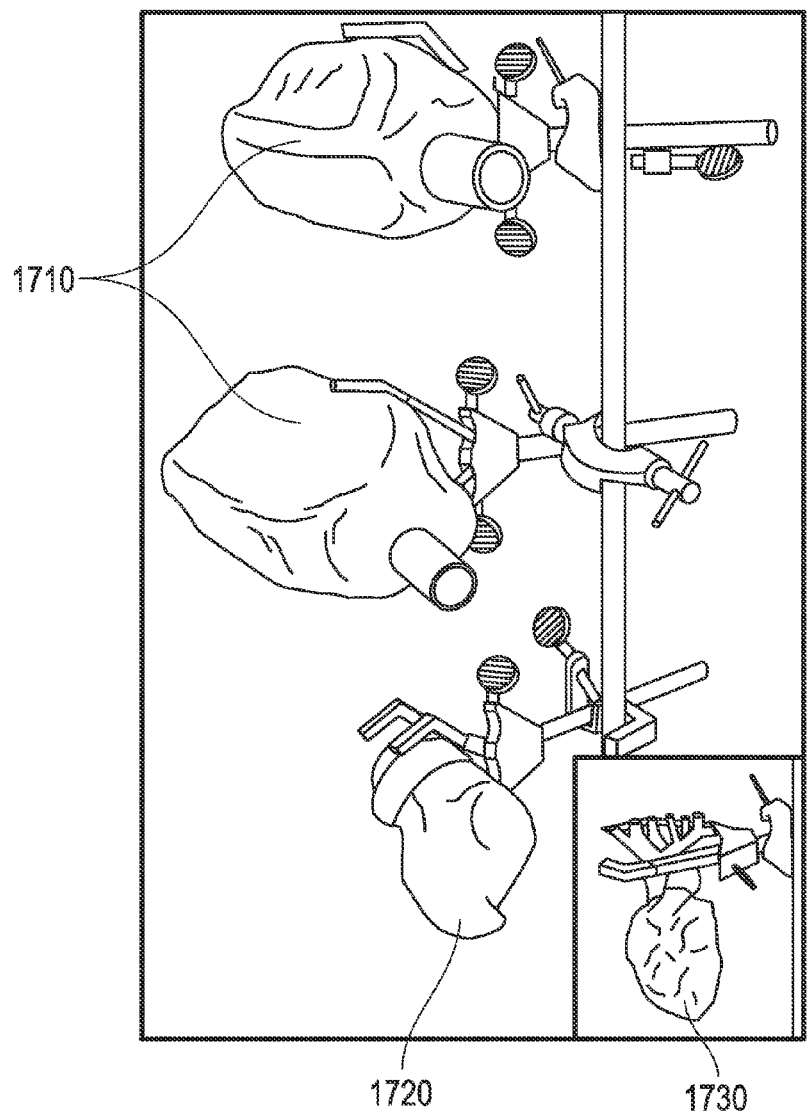
FIG. 17 is a photographic depiction of an embodiment of in vitro model anatomical components.

The interior of the model is sought to be reflective of the design drawing shown in FIG. 4. Here two large balloons on the edges of the cavity are to represent the lungs. These will be filled with air with modulating pressure. The heart representation can be visualized in the middle of the lungs. This rubber chamber is also able to modulate in volume. However, it is ideally filled with liquid. The chamber surrounding the heart is filled with a small amount of liquid that will represent the pericardial fluid. As the shapes of these irregular bodies are hard to find in commercially produced products, they were replicated using liquid latex. As can be seen in FIG. 9a, the lungs and heart were replicated using molds. For the heart, about 15-20 layers of liquid latex were painted on a life sized model of a heart and then the dried latex was removed. The form of the lungs was created by carving the shape of each lung on a styrofoam block. Then several layers of liquid latex were applied (FIG. 17). In addition there are tubes (bronchi) that allow for the air flow to be visualized. The lung and heart molds have been successfully tested in a hydraulic system for contractile motion.

Specifically, FIG. 17 is a photographic depiction of an embodiment of in vitro model anatomical components including molds 1710, 1720 and 1730.

Pressure control will be acquired by using a stepper motor (a unipolar stepper, 3.6V, 16 kgcm holding torque) to operate a linear actuator attached to an air pump. This air pump will not have a one way valve, but rather it will be able to both push and pull the air column. Two actuators will be used: one connected to the lung compartment and another connected to the liquid holding chamber connected to the heart. The mechanical schematic diagram for this device is shown in FIG. 18. The design was created to be ultimately a clear box that can be opened. On both faces of the box are linear actuator mechanisms that are controlled by stepper motors. It is connected to the stepper motor, which is controlled as described below. Two air pumps provide the pressure variations that simulate the pressures in the heart and lungs, as per the mechanism of FIG. 18.

Figure 19A:
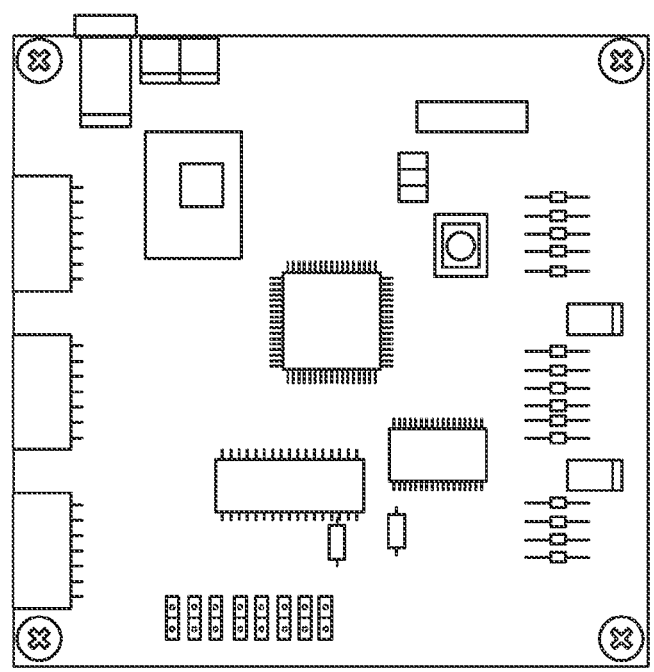
FIGS. 19A and 19B are photographic and schematic depictions, respectively, of a microcontroller.
Figure 19B:
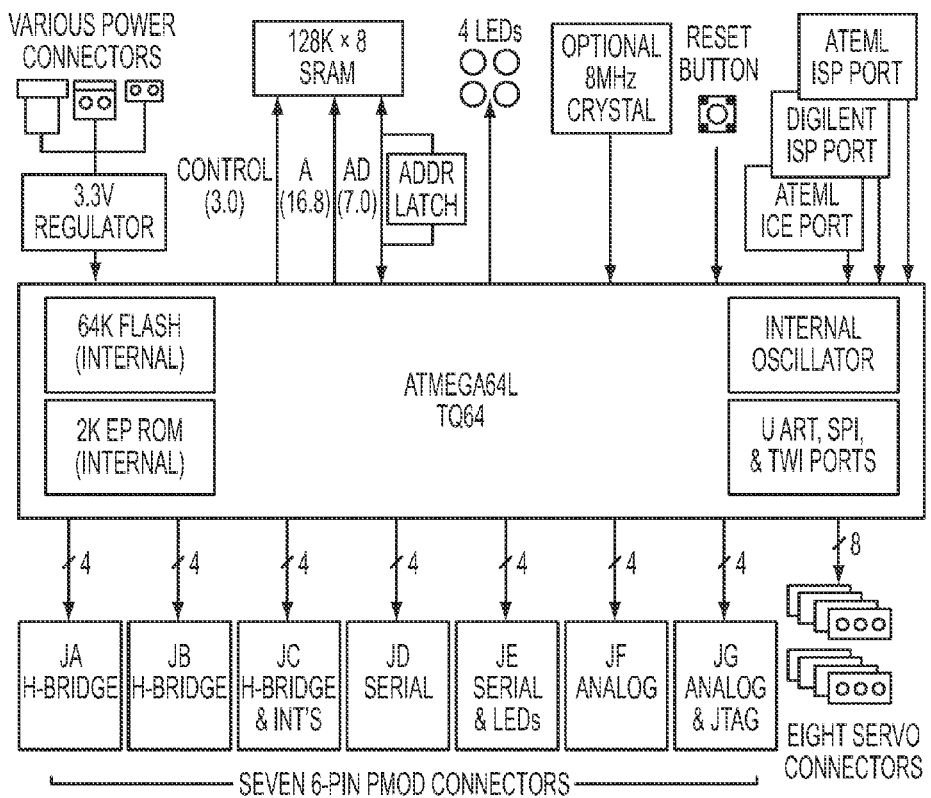

A microcontroller will be used to run the stepper motors. Specifically, the Cerebot system by Digilent Inc. will be used to provide serial interface with a computer for real time instructions as well as an H-Bridge connection to the unipolar stepper motor. An adaptive circuit will be made using four transistors to regulate power supply to the four leads of the stepper motor. Also, diodes will be used to counter the kickback current from the stepper motor to protect the microcontroller port. The microcontroller is equipped with an 8-bit AVR Microcontroller (FIGS. 19A & 19B) with 64K Bytes of in-system programmable flash memory. It is based on the ATmega64L processor. C will be used to construct the run time program. The Win-AVR will be used to convert the higher level C code into machine code/hexadecimal that will later be exported to the Cerebot (via a USB JTAG/SPI interface) using AVR programmer. The microcontroller will allow for preprogrammed or variable turns that will translate to pressure modulations.

Figure 20:
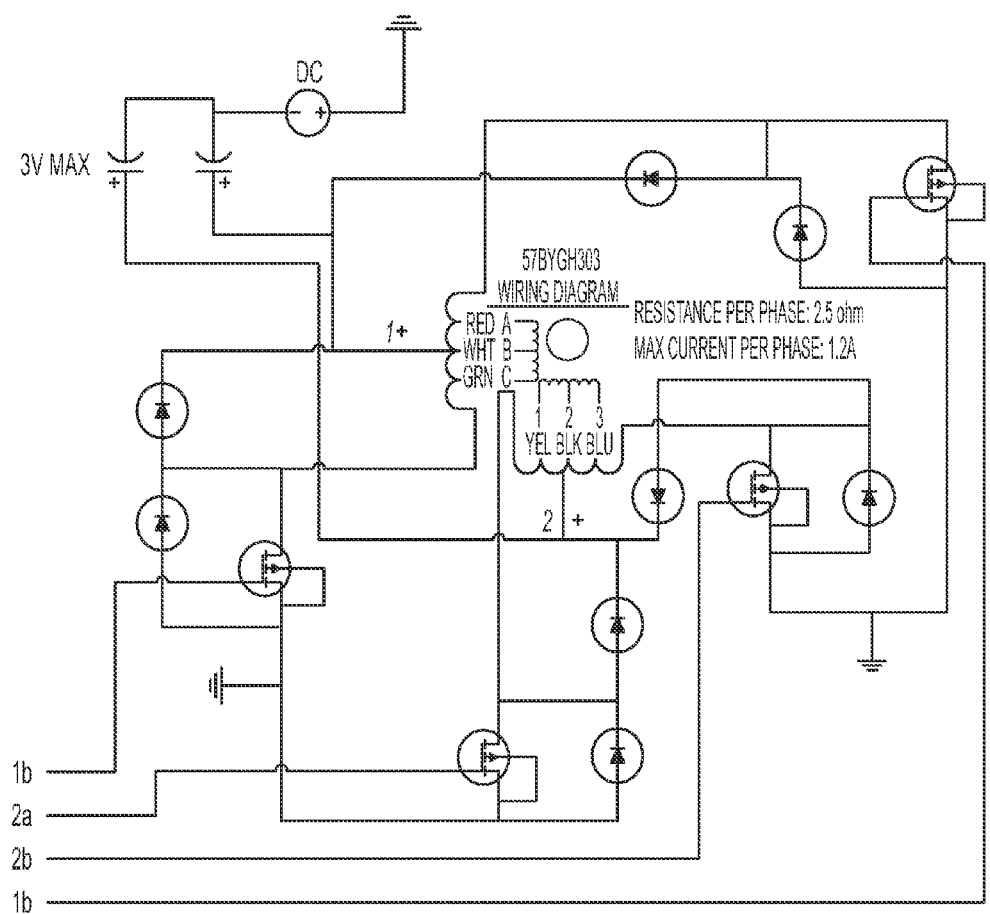
FIG. 20 is a schematic view of a circuit for controlling the current flow through the specific windings of a unipolar stepper motor.

The open source C program was adopted to implement the connection between computer via RS-232 COM port and the Cerebot COM port (JD) module. Ultimately, any PC connected to the microcontroller via an interface like Microsoft Hyperterminal is able to give the controller a specified commend set that allows the shifting of voltages in the JPC pins. The voltages can be switched from on or off varying from 0 to 3.2 V. This is important as the four pins are to be synchronously switched to operate the unipolar stepper motor. The steps of voltage were monitored via the oscilloscope. As there cannot be enough power delivered by these output ports to drive the stepper motor, a driver circuit was designed, built and tested (FIG. 20). This driver circuit ultimately allows for much larger currents (upwards of 2 A) flowing through the stepper motor on the switch command of several miliamperes. As the proposed circuit diagram shows in FIG. 20, power MOSFET transistors were used to grate the four conducting wires attached to the two unipolar stepper windings. The winding arrangement and properties are shown in the same figure. A stream of synchronized pulses from the microcontroller board to the transistor gates opens and closes them to allow current to flow accordingly. The operation of the circuit was successfully tested using LEDs, but as the threshold voltage for the gating of the MOSFTETs is one volt higher than that given by the controller, there needs to be a base voltage of about 1 V applied to all the gates before enough current opened for the operation of the stepper motor. Nevertheless, the stepper motor can be operated with great precision.

It is expected that as a needle is inserted through the insertion port at the sub-xyphoid site and into the thoracic cage, leading to the pericardial space, the physiologic pressure waveforms will be observed. Calibration of the pressure control systems will need to be done to reproduce these profiles. By modulating the volume of the lungs and the heart, we can generate a pressure profile in the thoracic cage and the pericardial space. These compartments are not directly being modulated by the pressure controllers, they are a consequence of them, therefore it is expected that the proposed procedure will be able to replicate the overlay of the thoracic and cardiac pressure waveforms.

Imperfections in the materials used may lead to inconsistent pressures. This is most notable in the thoracic cavity and it is important to keep an air tight chamber. The seals introduced by the diaphragm, upper (neck) seal and the sternum Plexiglas window leave ample room for air leaks. This leaking may severely dampen the pressure waveforms in the thoracic cavity. If air leaking is a great enough hindrance to the correct representation of the waveforms, then a feedback loop can be established with a third air pump connected directly to the thoracic cavity to counteract the leakage. The additional pump, however, can introduce significantly great complexities. A potential problem is the stepper motor itself, as in time it may overheat or even disrupt the electrical components running it. Therefore, other types of motors can also be incorporated. Another possible problem may be the actual air pumps themselves, as they may also lead to some certain extent. As they leak, this leakage is not compensated by the control program and a bias is introduced. The bias can be eliminated again by using feedback loops using a stationary pressure sensor.

Those skilled in the art will recognize the many significant advantages associated with this general approach by considering the general and specific embodiments of the invention as discussed above in the drawings and their descriptions.

Figure 21:
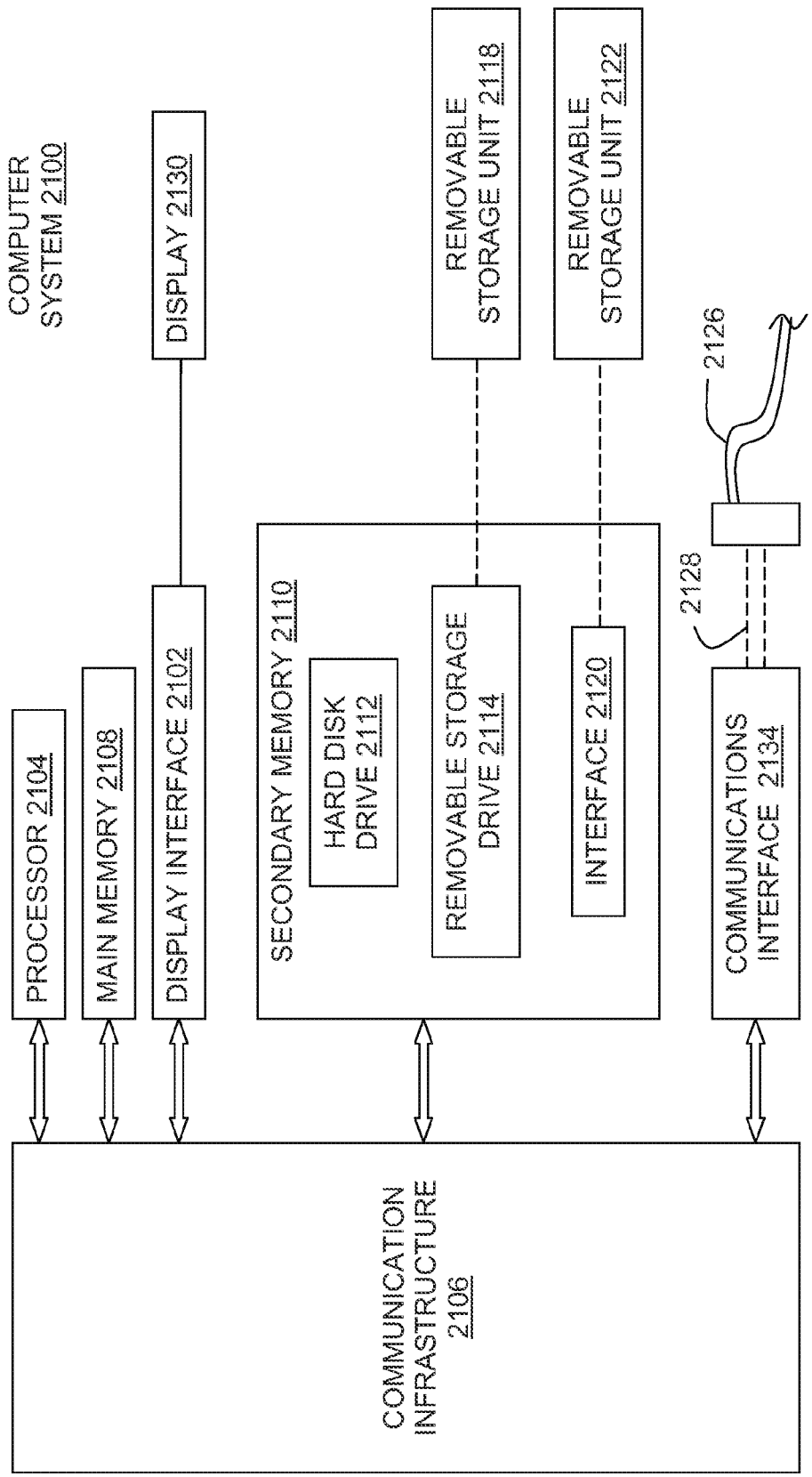
FIG. 21 is a schematic view of an aspect of an embodiment of a model communication system.
Figure 22:
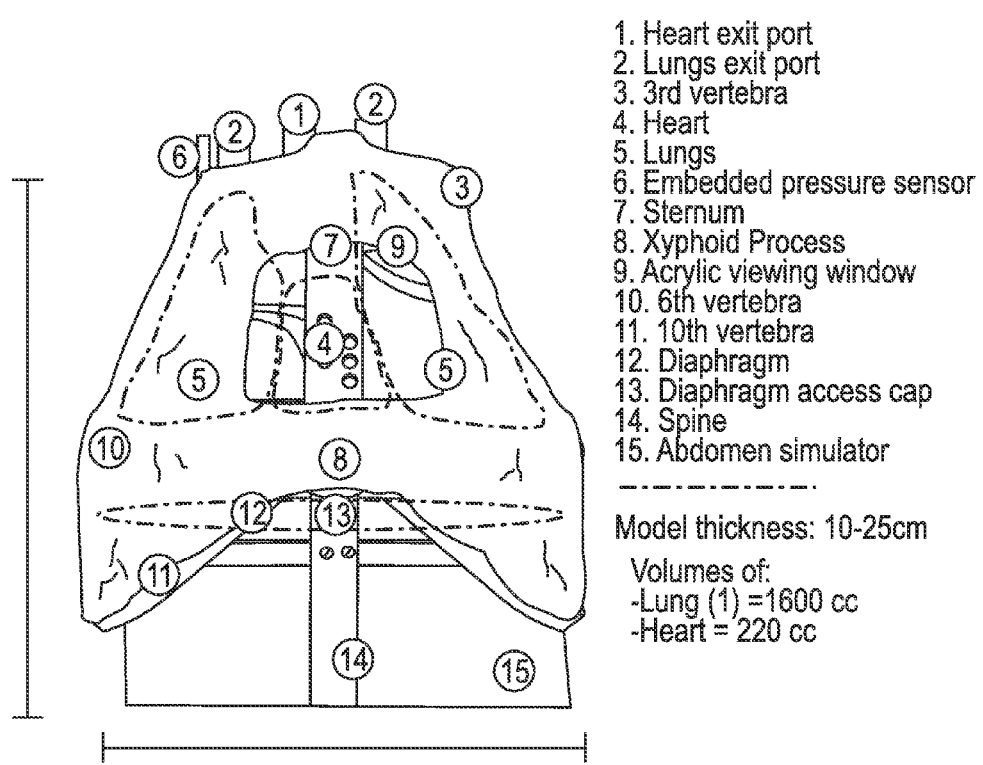
FIG. 22 is a photographic depiction of an embodiment of an in vitro model system.

FIG. 21 is a functional block diagram for a computer system 2100 for implementation of an exemplary embodiment or portion of an embodiment of present invention (or combinations of various embodiments in whole or in part of the present invention). For example, a method or system of an embodiment of the present invention may be implemented using hardware, software or a combination thereof and may be implemented in one or more computer systems or other processing systems, such as personal digit assistants (PDAs) equipped with adequate memory and processing capabilities. In an example embodiment, the invention was implemented in software running on a general purpose computer 2100 as illustrated in FIG. 21. The computer system 2100 may includes one or more processors, such as processor 2104. The Processor 2104 is connected to a communication infrastructure 2106 (e.g., a communications bus, cross-over bar, or network). The computer system 2100 may include a display interface 2102 that forwards graphics, text, and/or other data from the communication infrastructure 2106 (or from a frame buffer not shown) for display on the display unit 2130. Display unit 2130 may be digital and/or analog.

The computer system 2100 may also include a main memory 2108, preferably random access memory (RAM), and may also include a secondary memory 2110. The secondary memory 2110 may include, for example, a hard disk drive 2112 and/or a removable storage drive 2114, representing a floppy disk drive, a magnetic tape drive, an optical disk drive, a flash memory, etc. The removable storage drive 2114 reads from and/or writes to a removable storage unit 2118 in a well known manner. Removable storage unit 2118, represents a floppy disk, magnetic tape, optical disk, etc. which is read by and written to by removable storage drive 2114. As will be appreciated, the removable storage unit 2118 includes a computer usable storage medium having stored therein computer software and/or data.

In alternative embodiments, secondary memory 2110 may include other means for allowing computer programs or other instructions to be loaded into computer system 2100. Such means may include, for example, a removable storage unit 2122 and an interface 2120. Examples of such removable storage units/interfaces include a program cartridge and cartridge interface (such as that found in video game devices), a removable memory chip (such as a ROM, PROM, EPROM or EEPROM) and associated socket, and other removable storage units 2122 and interfaces 2120 which allow software and data to be transferred from the removable storage unit 2122 to computer system 2100.

The computer system 2100 may also include a communications interface 2124. Communications interface 2124 allows software and data to be transferred between computer system 2100 and external devices. Examples of communications interface 2124 may include a modem, a network interface (such as an Ethernet card), a communications port (e.g., serial or parallel, etc.), a PCMCIA slot and card, a modem, etc. Software and data transferred via communications interface 2124 are in the form of signals 2128 which may be electronic, electromagnetic, optical or other signals capable of being received by communications interface 2124. Signals 2128 are provided to communications interface 2124 via a communications path (i.e., channel) 2126. Channel 2126 (or any other communication means or channel disclosed herein) carries signals 2128 and may be implemented using wire or cable, fiber optics, blue tooth, a phone line, a cellular phone link, an RF link, an infrared link, wireless link or connection and other communications channels.

In this document, the terms "computer program medium" and "computer usable medium" are used to generally refer to media or medium such as various software, firmware, disks, drives, removable storage drive 2114, a hard disk installed in hard disk drive 2112, and signals 2128. These computer program products ("computer program medium" and "computer usable medium") are means for providing software to computer system 2100. The computer program product may comprise a computer useable medium having computer program logic thereon. The invention includes such computer program products. The "computer program product" and "computer useable medium" may be any computer readable medium having computer logic thereon.

Computer programs (also called computer control logic or computer program logic) are may be stored in main memory 2108 and/or secondary memory 2110. Computer programs may also be received via communications interface 2124. Such computer programs, when executed, enable computer system 2100 to perform the features of the present invention as discussed herein. In particular, the computer programs, when executed, enable processor 2104 to perform the functions of the present invention. Accordingly, such computer programs represent controllers of computer system 2100.

In an embodiment where the invention is implemented using software, the software may be stored in a computer program product and loaded into computer system 2100 using removable storage drive 2114, hard drive 2112 or communications interface 2124. The control logic (software or computer program logic), when executed by the processor

2104, causes the processor 1304 to perform the functions of the invention as described herein.

In another embodiment, the invention is implemented primarily in hardware using, for example, hardware components such as application specific integrated circuits (ASICs). Implementation of the hardware state machine to perform the functions described herein will be apparent to persons skilled in the relevant art(s).

In yet another embodiment, the invention is implemented using a combination of both hardware and software.

In an example software embodiment of the invention, the methods described above may be implemented in SPSS control language or C++ programming language, but could be implemented in other various programs, computer simulation and computer-aided design, computer simulation environment, MATLAB, or any other software platform or program, windows interface or operating system (or other operating system) or other programs known or available to those skilled in the art.

The devices, systems, compositions, modules, computer program products, and methods of various embodiments of the invention disclosed herein may utilize aspects disclosed in the following references, applications, publications and patents and which are hereby incorporated by reference herein in their entirety:

1. U.S. Pat. No. 6,874,501 B1, Estetter, et al., "Lung Simulator", Apr. 5, 2005.
2. U.S. Pat. No. 6,428,323 B1, Pugh, C., "Medical Examination Teaching System", Aug. 6, 2002.
3. U.S. Pat. No. 6,273,728 B1, van Meurs, et al., "Life Support Simulation System Simulating Human Physiological Parameters", Aug. 14, 2001.
4. U.S. Pat. No. 5,428,323, Geissler, et al., "Device for Compensation For Temperature-Dependent Volume Changes in a Waveguide", Jun. 27, 1995.
5. U.S. Pat. No. 7,510,398 B1, Thornton, W., "Apparatus for Simulating a Pulse and Heart Beat and Methods For Using Same To Train Medical Professionals", Mar. 31, 2009.
6. U.S. Patent Application Publication No. US 2009/0111080 A1, Chen, et al., "Medical Simulation System and Method", Apr. 30, 2009.
7. U.S. Pat. No. 6,921,267 B2, van Oostrom, et al., "Lung Simulator For An Integrated Human Patient Simulator", Jul. 26, 2005.
8. U.S. Pat. No. 5,584,701, Lampotang, et al., "Self Regulating Lung For Simulated Medical Procedures", Dec. 17, 1996.
9. U.S. Pat. No. 5,800,197, Bailey, B., "System For Trainingt Persons To Perform Minimally Invasive Surgical Procedures", Sep. 1, 1998.
10. U.S. Pat. No. 4,167,070, Orden, B., "Educational Lung Simulator", Sep. 11, 1979.
11. U.S. Pat. No. 6,062,865, Bailey, B., "System For Training Persons To Perform Minimally Invasive Surgical Procedures", May 16, 2000.
12. U.S. Pat. No. 6,267,599 B1, Bailey, B., "System For Training Persons To Perform Minimally Invasive Surgical Procedures", Jul. 31, 2001.
13. U.S. Pat. No. 7,021,940 B2, Morris, et al., "Patient Simulator Manikin And System", Apr. 4, 2006.
14. U.S. Pat. No. 6,336,812 B1, Cooper, et al., "Clinical And/Or Surgical Training Apparatus", Jan. 8, 2002.
15. U.S. Pat. No. 6,234,804 B1, Yong, P., "Thoracic Training Model For Endoscopic Cardiac Surgery", May 22, 2001.
16. U.S. Pat. No. 6,007,342, Tjelsen, Ø., "Pulse Device For Creating A Simulated Feelable And Recognition of Pulse.
17. JP Patent No. 5-27113, April 1993
18. JP Patent No. 2990602, October 1999
19. "A Computer-Controlled Patient Simulator", J. S. Denson, M. D., and Stephen Abrahamson, Ph.D., JAMA (Apr. 21, 1969), vol. 208, p. 3, pp. 504-508.
20. U.S. Pat. No. 6,175,768 B1, Arndt et al., "In Vivo Simulator for Microwave Treatment", Jan. 16, 2001.
21. PCT International Application No. Serial No. PCT/US2008/056643, filed Mar. 12, 2008, entitled, "Access Needle Pressure Sensor Device and Method of Use" and corresponding U.S. patent application Ser. No. 12/530,830 filed Sep. 11, 2009.
22. PCT International Application No. Serial No. PCT/US2008/056816, filed Mar. 13, 2008, entitled, "Epicardial Ablation Catheter and Method of Use" and corresponding U.S. patent application Ser. No. 12/530,938 filed Sep. 11, 2009.
23. PCT International Application No. Serial No. PCT/US2008/057626, filed Mar. 20, 2008, entitled, "Electrode Catheter for Ablation Purposes and Related Method Thereof" and corresponding U.S. patent application Ser. No. 12/532,233 filed Sep. 21, 2009.
24. PCT international Application No. Serial No. PCT/US2008/082835, filed Nov. 7, 2008, entitled, "Steerable Epicardial Pacing Catheter System Placed Via the Subxiphoid Process," and corresponding U.S. patent application Ser. No. 12/741,710 filed May 6, 2010.

Unless clearly specified to the contrary, there is no requirement for any particular described or illustrated activity or element, any particular sequence or such activities, any particular size, speed, material, duration, contour, dimension or frequency, or any particularly interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. It should be appreciated that aspects of the present invention may have a variety of sizes, contours, shapes, compositions and materials as desired or required.

In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the following claims, including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

We claim:

1. An in vitro model system, said system comprising:
a thoracic cavity;
lungs disposed within said thoracic cavity;
said lungs configured to contain a lung fluid having a lung pressure-frequency profile;
a heart disposed within said thoracic cavity;
said heart configured to contain a cardiac fluid having a cardiac pressure frequency profile; and
a pericardium disposed within said thoracic cavity and configured to at least partially surround said heart;
said pericardium configured to contain—between said pericardium and said heart—a pericardial fluid having a pericardial pressure-frequency profile.

2. The model system of claim 1, further comprising:
a model communication system for providing at least one of the following: the lung pressure-frequency profile, the cardiac pressure-frequency profile, and/or the pericardial pressure-frequency profile.

3. The model system of claim 2, wherein:
said model communication system is configured to pump at least one of the following: the lung fluid, the cardiac fluid, and/or the pericardial fluid.

4. The model system of claim 2, further comprising:
a controller;
a motor;
an actuator; and
a pumping mechanism,
wherein:
said controller is configured to receive data representing the at least one the pressure frequency profile and communicate with said motor;
said motor is configured to communicate with said controller and said actuator;
said actuator is configured to communicate with said motor and said pumping mechanism; and
said pumping mechanism is configured to communicate with said actuator and at least one of the following: the lung fluid, the cardiac fluid, and/or the pericardial fluid.

5. The model system of claim 2, wherein the at least one pressure-frequency profiles is a function of: respiratory parameters and/or cardiac parameters.

6. The model system of claim 1, wherein:
the lung pressure-frequency profile mimics a subject breathing or intubation waveform;
the cardiac pressure-frequency profile mimics a subject cardiac waveform; and
the pericardial pressure-frequency profile mimics the sum of at least:
a component or damped component of the subject breathing or intubation waveform; and
a component or damped component of the subject cardiac waveform.

7. The model system of claim 1, further comprising:
a fluid source;
an aperture in at least one of said lungs, said heart, or said pericardium; and
a sealed connective apparatus between said fluid source and said aperture in at least one of said lungs, said heart, or said pericardium.

8. The model system of claim 1, further comprising:
an access device configured to enter one or more of said thoracic cavity, said lungs, said heart, and/or said pericardium,
wherein said system is configured for testing said access device or training a user of said access device.

9. The model system of claim 8, wherein said access device comprises at least one of a surgical instrument, a needle, a probe, a catheter, or a minimally invasive device, and wherein said access device is further configured to sense a pressure profile and/or a pressure-frequency profile.

10. The model system of claim 1, wherein:
said pericardium is sealed; and
the pericardial pressure-frequency profile results from communication of said pericardium and/or the pericardial fluid with said lungs and/or said heart.

11. An in vitro model system, said system comprising:
a set of anatomical components configured to contain at least one fluid;
at least one pressure-frequency profile; and
a model communication system for providing said at least one pressure-frequency profile to said at least one fluid,
wherein said set of anatomical components comprises:
a lung fluid having a lung pressure-frequency profile;
a cardiac fluid having a cardiac pressure-frequency profile; and
a pericardial fluid having a pericardial pressure-frequency profile.

12. The model system of claim 11, wherein:
said set of anatomical components comprises at least one or more of the following: a thoracic cavity, lungs, a heart, a pericardium, a spine, one or more ribs, a sternum, and/or skin.

13. The model system of claim 11, wherein:
the lung pressure-frequency profile mimics a subject breathing or intubation waveform;
the cardiac pressure-frequency profile mimics a subject cardiac waveform; and
the pericardial pressure-frequency profile mimics the sum of at least:
a component or damped component of the subject breathing or intubation waveform; and
a component or damped component of the subject cardiac waveform.

14. The model system of claim 11, further comprising:
a controller;
a motor;
an actuator; and
a pumping mechanism,
wherein:
- said controller configured to receive data representing said at least one pressure frequency profile and to communicate with said motor;
- said motor configured to communicate with said controller and said actuator;
- said actuator configured to communicate with said motor and said pumping mechanism; and
- said pumping mechanism is configured to communicate with said actuator and the at least one fluid.

15. An in vitro modeling method, said method comprising:
providing a thoracic cavity;
providing lungs disposed within said thoracic cavity, wherein said lungs contain a lung fluid;
applying a lung pressure-frequency profile to the lung fluid;
providing a heart disposed within said thoracic cavity, wherein said heart contains a cardiac fluid;
applying a cardiac pressure-frequency profile to said cardiac fluid;
providing a pericardium disposed within said thoracic cavity, wherein said pericardium at least partially surrounds said heart, and wherein said pericardium contains a pericardial fluid between said pericardium and said heart; and
applying a pressure-frequency profile to said pericardial fluid.

16. The method of claim 15, wherein said application of said lung pressure-frequency profile, said cardiac pressure-frequency profile, and said pericardial pressure-frequency profile comprises: pumping at least one of the following: the lung fluid, the cardiac fluid, or the pericardial fluid.

17. The method of claim 15, wherein:
the lung pressure-frequency profile mimics a subject breathing or intubation waveform;
the cardiac pressure-frequency profile mimics a subject cardiac waveform; and
the pericardial pressure-frequency profile mimics the sum of at least:
- a component or damped component of the subject breathing or intubation waveform; and
- a component or damped component of the subject cardiac waveform.

18. The method of claim 15, further comprising:
providing an access device that enters one or more of said thoracic cavity, said lungs, said heart, and/or said pericardium;
sensing at least one of a pressure profile and a pressure-frequency profile with said access device.

* * * * *